US009974464B2

(12) United States Patent
Shiodera et al.

(10) Patent No.: US 9,974,464 B2
(45) Date of Patent: May 22, 2018

(54) IMAGE PROCESSING APPARATUS AND MAGNETIC RESONANCE IMAGING APPARATUS

(71) Applicant: TOSHIBA MEDICAL SYSTEMS CORPORATION, Otawara-shi, Tochigi (JP)

(72) Inventors: Taichiro Shiodera, Tokyo (JP); Shuhei Nitta, Tokyo (JP); Tomoyuki Takeguchi, Kanagawa (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 179 days.

(21) Appl. No.: 14/937,178

(22) Filed: Nov. 10, 2015

(65) Prior Publication Data

US 2016/0058319 A1     Mar. 3, 2016

Related U.S. Application Data

(63) Continuation of application No. PCT/JP2014/062522, filed on May 9, 2014.

(30) Foreign Application Priority Data

May 10, 2013   (JP) ................................ 2013-100699

(51) Int. Cl.
    *G06T 7/00*     (2017.01)
    *A61B 5/055*     (2006.01)
    (Continued)

(52) U.S. Cl.
    CPC ............ *A61B 5/055* (2013.01); *A61B 5/0042* (2013.01); *A61B 5/4064* (2013.01);
    (Continued)

(58) Field of Classification Search
    CPC ..... A61B 5/055; A61B 5/0042; A61B 5/4064; G06F 19/321; G06T 1/20
    See application file for complete search history.

(56) References Cited

U.S. PATENT DOCUMENTS 9,042,961 B2 *   5/2015   Miyazaki ............... A61B 5/055
                                                           600/419
2009/0005670 A1     1/2009   Ichinose et al.
                                   (Continued)

FOREIGN PATENT DOCUMENTS

JP     2006-158791     6/2006
JP     2009-028525     2/2009
               (Continued)

OTHER PUBLICATIONS

Kurtcuoglu, Vartan, et al. "Reconstruction of cerebrospinal fluid flow in the third ventricle based on MRI data." Medical Image Computing and Computer-Assisted Intervention—MICCAI 2005 (2005): 786-793.*

(Continued)

*Primary Examiner* — Kim Vu
*Assistant Examiner* — Molly Delaney
(74) *Attorney, Agent, or Firm* — Nixon & Vanderhye P.C.

(57) ABSTRACT

An image processing apparatus according to an embodiment includes a processor and a memory. The memory stores processor-executable instructions that, when executed by the processor, cause the processor to: receive an input of information designating an observation target; extract, from each of magnetic resonance (MR) images included in an MR image group collected by applying a tagging pulse to a region where a fluid flows, a group of regions of the fluid; analyze, by an analyzing method associated with the observation target, the group of regions of the fluid extracted from each of the MR images, thereby deriving an index indicating (Continued)

a dynamic state of the fluid; and cause the index to be displayed on a display.

10 Claims, 25 Drawing Sheets

(51) Int. Cl.
    *G01R 33/563*    (2006.01)
    *A61B 5/00*    (2006.01)
    *G06T 1/20*    (2006.01)
    *G06F 19/00*    (2018.01)
    *G01R 33/54*    (2006.01)
    *A61B 5/03*    (2006.01)

(52) U.S. Cl.
    CPC ..... *G01R 33/56308* (2013.01); *G06F 19/321* (2013.01); *G06T 1/20* (2013.01); *G06T 7/0016* (2013.01); *A61B 5/031* (2013.01); *A61B 5/742* (2013.01); *G01R 33/546* (2013.01); *G06T 2207/20224* (2013.01); *G06T 2207/30016* (2013.01); *G06T 2210/41* (2013.01)

(56) References Cited

U.S. PATENT DOCUMENTS

| | | |
|---|---|---|
| 2010/0087730 A1 | 4/2010 | Yamada et al. |
| 2010/0198053 A1* | 8/2010 | Miyazaki ............... A61B 5/055 600/419 |
| 2012/0095326 A1 | 4/2012 | Miyazaki |
| 2012/0302871 A1 | 11/2012 | Yamada et al. |
| 2013/0154645 A1* | 6/2013 | Furudate ................ G01R 33/54 324/314 |
| 2013/0289387 A1* | 10/2013 | Shiodera ................ A61B 5/055 600/419 |

FOREIGN PATENT DOCUMENTS

| | | |
|---|---|---|
| JP | 2009-279218 | 12/2009 |
| JP | 2010-88515 | 4/2010 |
| JP | 2010-201154 | 9/2010 |
| WO | WO 2014/123086 | 8/2014 |

OTHER PUBLICATIONS

Gerber, Meredith L. Graphical interface for quantitative monitoring of 3D MRI data. Diss. Massachusetts Institute of Technology, 2005.*
International Search Report for PCT/JP2014/062522, dated Jun. 24, 2014, 4 pages.
Written Opinion of the ISA for PCT/JP2014/062522, dated Jun. 24, 2014, 4 pages.
English translation of the Written Opinion of the International Searching Authority in PCT/JP2014/062522 dated Jun. 24, 2014.

* cited by examiner

| Observation site | |
|---|---|
| Monro | |
| Prepontine cistern | ▼ |
| Aqueduct | |
| ... | |
| Other | |

IMAGE PROCESSING APPARATUS AND MAGNETIC RESONANCE IMAGING APPARATUS

CROSS-REFERENCE TO RELATED APPLICATIONS

This application is a continuation of PCT international application Ser. No. PCT/JP2014/062522 filed on May 9, 2014 which designates the United States, incorporated herein by reference, and which claims the benefit of priority from Japanese Patent Applications No. 2013-100699, filed on May 10, 2013, incorporated herein by reference.

FIELD

Embodiments described herein relate generally to an image processing apparatus and a magnetic resonance imaging apparatus.

BACKGROUND

Magnetic resonance imaging is an imaging method of generating an image from a magnetic resonance (MR) signal generated associated with magnetic excitation by a radio frequency (RF) pulse having the Larmor frequency for nuclear spins of a subject placed in a static magnetic field. In the field of the magnetic resonance imaging, non-contrast magnetic resonance angiography (MRA) has been known as a method of acquiring an image of a blood vessel, without using a contrast agent.

DETAILED DESCRIPTION

An image processing apparatus according to an embodiment includes a processor and a memory. The memory stores processor-executable instructions that, when executed by the processor, cause the processor to: receive an input of information designating an observation target; extract, from each of magnetic resonance (MR) images included in an MR image group collected by applying a tagging pulse to a region where a fluid flows, a group of regions of the fluid; analyze, by an analyzing method associated with the observation target, the group of regions of the fluid extracted from each of the MR images, thereby deriving an index indicating a dynamic state of the fluid; and cause the index to be displayed on a display.

Hereinafter, an image processing apparatus and a magnetic resonance imaging apparatus (hereinafter referred to as "MRI apparatus" as appropriate) according to embodiments will be described with reference to accompanying drawings. Embodiments are not limited, however, to the embodiments described below. The contents described in each of the following embodiments can, in principle, be applied to other embodiments in the same manner.

First Embodiment

Figure 1:
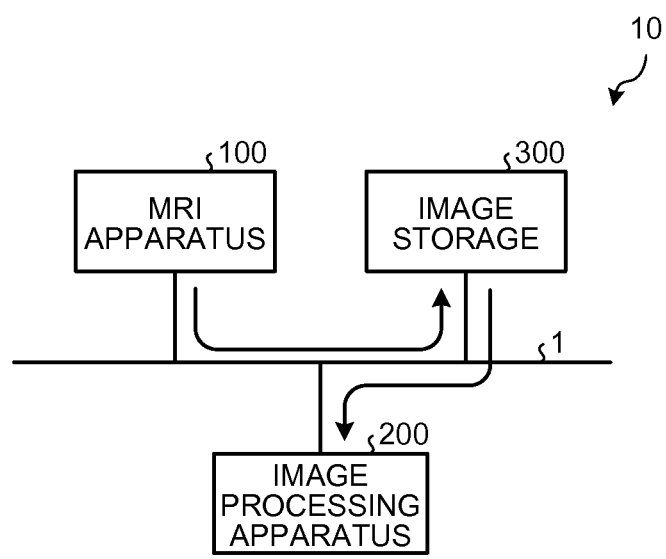
FIG. 1 is a block diagram illustrating an image processing system according to a first embodiment.

FIG. 1 is a block diagram of an image processing system 10 according to a first embodiment. As illustrated in FIG. 1, the image processing system 10 according to the first embodiment includes an MRI apparatus 100, an image processing apparatus 200, and an image storage apparatus 300. These apparatuses are connected to be able to communicate with each other via a network 1 such as an in-hospital local area network (LAN) and the Internet.

In the first embodiment, the MRI apparatus 100 images a cerebrospinal fluid (hereinafter referred to as "CSF" as appropriate) of a subject P to acquire a CSF image group, and stores the acquired image data in the image storage apparatus 300 of a picture archiving and communication system (PACS). By contrast, the image processing apparatus 200 acquires image data of the CSF image group from the MRI apparatus 100 or the image storage apparatus 300, or via a storage medium, thereby performing various processing for evaluation of a dynamic state of the CSF using the acquired image data. The image processing apparatus 200 is an apparatus of various types such as a workstation, a viewer, and an electronic medical record system.

Figure 2:
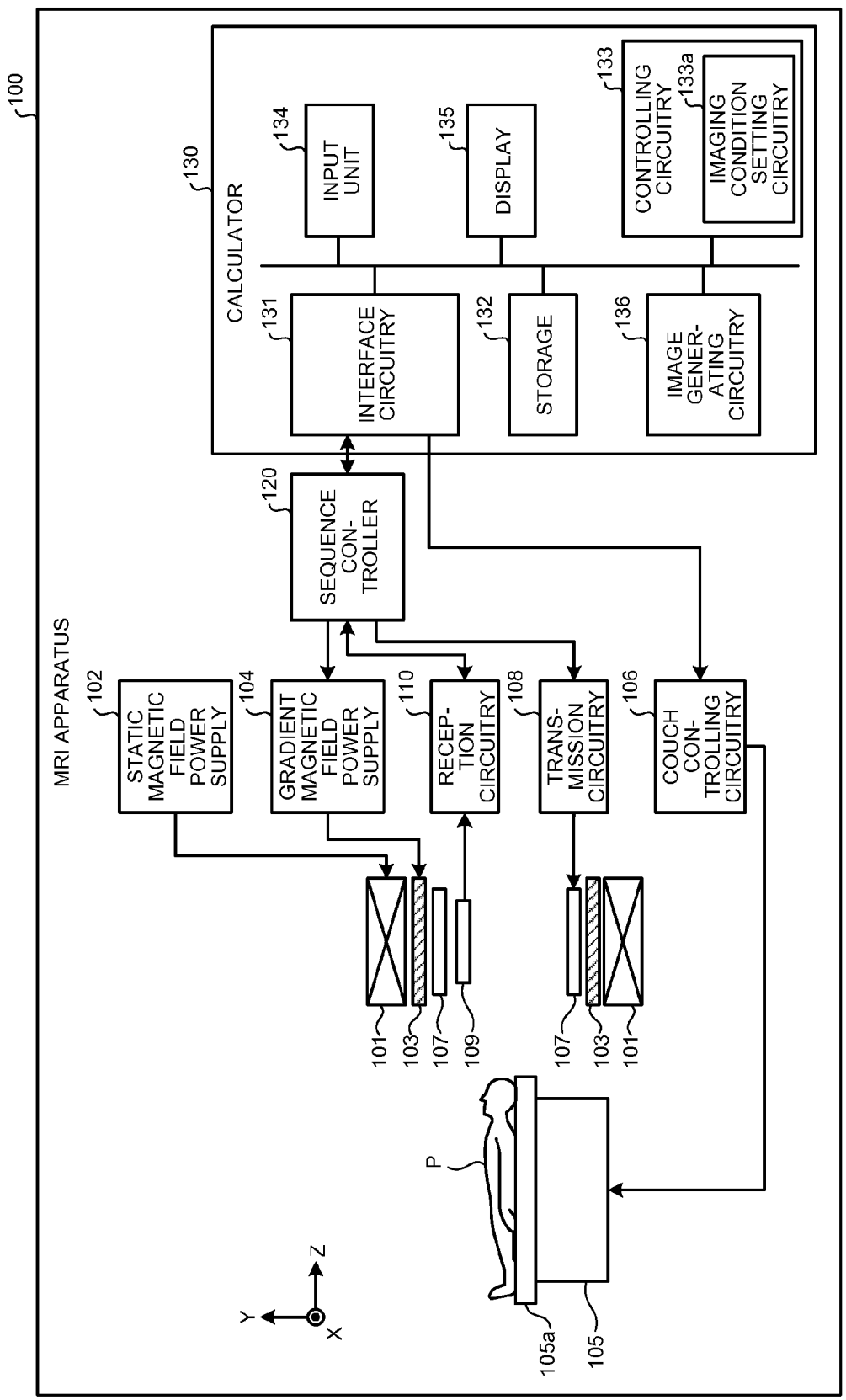
FIG. 2 is a block diagram of a magnetic resonance imaging (MRI) apparatus in the first embodiment.

FIG. 2 is a block diagram illustrating the MRI apparatus 100 according to the first embodiment. As illustrated in FIG. 2, the MRI apparatus 100 includes a static magnetic field magnet 101, a static magnetic field power supply 102, a gradient coil 103, a gradient magnetic field power supply 104, a couch 105, couch controlling circuitry 106, a transmitting coil 107, transmission circuitry 108, a receiving coil 109, reception circuitry 110, sequence controlling circuitry 120, and a calculator 130. The MRI apparatus 100 does not include a subject P (e.g., a human body). FIG. 1 is merely an example. The sequence controlling circuitry 120 and the calculator 130 may be configured integrally or separately as appropriate, for example.

The static magnetic field magnet 101 is a magnet in a hollowed cylindrical shape that generates a static magnetic field in its interior space. The static magnetic field magnet 101 is a superconducting magnet, for example, that receives a power supply from the static magnetic field power supply 102 to excite the magnetic field. The static magnetic field power supply 102 supplies the static magnetic field magnet 101 with an electric current. The static magnetic field magnet 101 may be a permanent magnet, in which case the MRI apparatus 100 need not comprise the static magnetic field power supply 102. Alternatively, the static magnetic field power supply 102 may be provided separately from the MRI apparatus 100.

The gradient coil 103 is a coil in a hollowed cylindrical shape and disposed inside of the static magnetic field magnet 101. The gradient coil 103 includes three coils each corresponding to X, Y, and Z axes which are orthogonal to each other. Each of the three coils individually receives an electric current supply from the gradient magnetic field power supply 104 and generates gradient magnetic fields having different magnetic field strengths along the X, Y and Z axes, respectively. The gradient magnetic fields along the X, Y, and Z axes generated by the gradient coil 103 are, for example, a gradient magnetic field for slice encoding Gs, a gradient magnetic field for phase encoding Ge, and a gradient magnetic field for readout Gr, respectively. The gradient magnetic field power supply 104 supplies the gradient coil 103 with an electric current.

The couch 105 includes a couchtop 105a on which a subject P is placed. The couch 105 inserts the couchtop 105a with the subject P placed thereon into a hollow (an opening for imaging) of the gradient coil 103 under the control of the couch controlling circuitry 106. The couch 105 is usually provided so as to have its longitudinal direction parallel to the central axis of the static magnetic field magnet 101. The couch controlling circuitry 106 drives the couch 105 to move the couchtop 105a in its longitudinal direction and its vertical direction under the control of the calculator 130.

The transmitting coil 107 disposed inside of the gradient coil 103 receives RF pulses supplied from the transmission circuitry 108 and generates a high-frequency magnetic field. The transmission circuitry 108 supplies the transmitting coil 107 with the RF pulses corresponding to the Larmor frequency determined by the type of the target atom and the magnetic field strength.

The receiving coil 109 disposed inside of the gradient coil 103 receives an MR signal emitted from the subject P under the influence of the high-frequency magnetic field. Upon receiving the MR signal, the receiving coil 109 outputs the received MR signal to the reception circuitry 110.

The transmitting coil 107 and the receiving coil 109 are described above merely for exemplary purpose. One or more coils may be used out of the coils such as a coil including a transmitting function only, a coil including a receiving function only, or a coil including transmitting and receiving functions.

The reception circuitry 110 detects the MR signal output from the receiving coil 109 and generates a piece of MR data based on the detected MR signal. Specifically, the reception circuitry 110 converts the MR signal output from the receiving coil 109 into a digital signal to generate the MR data. The reception circuitry 110 transmits the generated MR data to the sequence controlling circuitry 120. It is noted that the reception circuitry 110 may be provided on the side of a gantry device including the static magnetic field magnet 101 and the gradient coil 103.

The sequence controlling circuitry 120 drives the gradient magnetic field power supply 104, the transmission circuitry 108, and the reception circuitry 110 based on sequence information transmitted from the calculator 130, thereby capturing an image of the subject P. The sequence information defines the procedure for imaging. The sequence information defines the following, for example: the strength and the timing of the current supplied by the gradient magnetic field power supply 104 to the gradient coil 103; the strength of the RF pulse supplied by the transmission circuitry 108 to the transmitting coil 107 or the application timing of the RF pulse; and the timing of detecting the MR signal by the reception circuitry 110. For example, the sequence controlling circuitry 120 is an integrated circuit such as an application specific integrated circuit (ASIC) and a field programmable gate array (FPGA). For another example, the sequence controlling circuitry 120 is an electronic circuit such as a central processing unit (CPU) and a micro processing unit (MPU).

After the sequence controlling circuitry 120 drives the gradient magnetic field power supply 104, the transmission circuitry 108, and the reception circuitry 110 to capture an image of the subject P, thereby receiving the MR data from the reception circuitry 110, the sequence controlling circuitry 120 transfers the received MR data to the calculator 130.

The calculator 130 controls the MRI apparatus 100 totally and generates an image. The calculator 130 includes interface circuitry 131, storage 132, controlling circuitry 133, an input unit 134, a display 135, and image generating circuitry 136.

The interface circuitry 131 transmits the sequence information to the sequence controlling circuitry 120 and receives the MR data from the sequence controlling circuitry 120. After receiving the MR data, the interface circuitry 131 stores the received MR data in the storage 132. The MR data stored in the storage 132 is disposed in the k-space by the controlling circuitry 133. This operation allows the storage 132 to store k-space data therein.

The storage 132 stores therein the MR data received by the interface circuitry 131, the k-space data disposed in the k-space by the controlling circuitry 133, and the image data generated by the image generating circuitry 136. For example, the storage 132 is a semiconductor memory device such as a random access memory (RAM) and a flash memory, or alternatively a hard disk, an optical disc, or the like.

The input unit 134 receives various types of instructions and information input from an operator. For example, the input unit 134 is a pointing device such as a mouse and a trackball, or an input device such as a keyboard. The display 135 displays a graphical user interface (GUI) for receiving an input of imaging conditions and an image generated by the image generating circuitry 136 under the control of the controlling circuitry 133. The display 135 is a display device such as a liquid crystal display device.

The controlling circuitry 133 performs an overall control of the MRI apparatus 100, thereby controlling capturing, generation, and display of images. As illustrated in FIG. 2, the controlling circuitry 133 includes imaging condition setting circuitry 133a. The imaging condition setting circuitry 133a receives an input of imaging conditions on the GUI, and generates sequence information in accordance with the received imaging conditions. The imaging condition setting circuitry 133a also transmits the generated sequence information to the sequence controlling circuitry 120. For example, the controlling circuitry 133 is an integrated circuit such as an ASIC and an FPGA, or an electronic circuit such as a CPU and an MPU.

The image generating circuitry 136 reads the k-space data from the storage 132 and executes reconfiguration processing on the read k-space data such as the Fourier transform, thereby generating an image.

Figure 3:
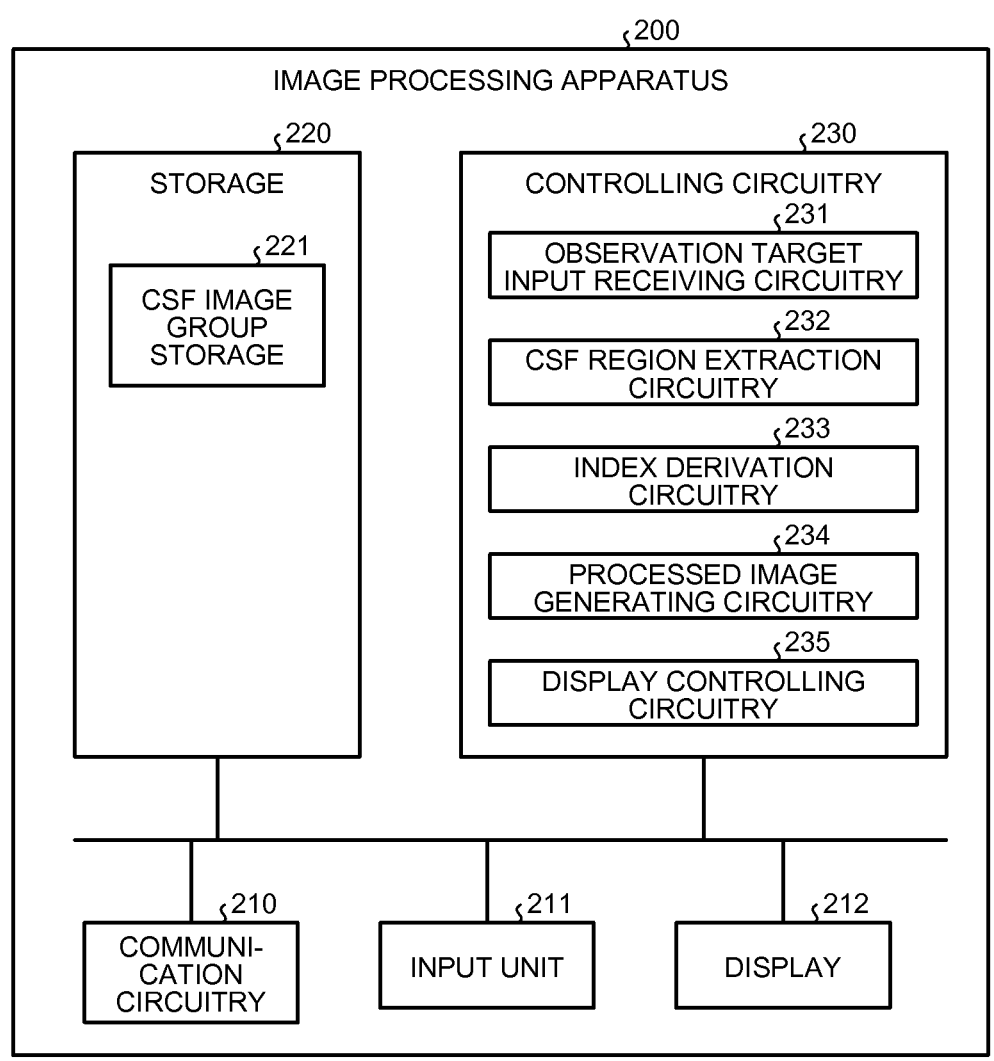
FIG. 3 is a block diagram of an image processing apparatus in the first embodiment.

FIG. 3 is a block diagram of the image processing apparatus 200 according to the first embodiment. As illustrated in FIG. 3, the image processing apparatus 200 includes communication circuitry 210, an input unit 211, a display 212, storage 220, and controlling circuitry 230.

The communication circuitry 210 performs communications between the MRI apparatus 100 and the image storage apparatus 300. For example, the communication circuitry 210 is a communication interface such as a LAN card. The input unit 211 receives an input of various types of instructions and information from the operator. The input unit 211 is a pointing device such as a mouse and a trackball, or an input device such as a keyboard. The display 212 displays a GUI for receiving an input of an observation target (such as an observation target region and an observation target region), and displays information (such as an analysis result display screen) indicating the dynamic state of the CSF. The display 211 is a display device such as a liquid crystal display device and a touch panel.

The storage 220 includes CSF image group storage 221. The CSF image group storage 221 stores therein image data of a CSF image group acquired via the MRI apparatus 100, the image storage apparatus 300, or a storage medium. The image data stored in the CSF image group storage 221 serves as an object of processing performed by the controlling circuitry 230 described later. The storage 220 is, for example, a semiconductor memory device such as a RAM and a flash memory, or alternatively a hard disk, an optical disc, or the like.

The controlling circuitry 230 includes an observation target input receiving circuitry 231, a CSF region extraction circuitry 232, an index derivation circuitry 233, a processed image generating circuitry 234, and display controlling circuitry 235. The controlling circuitry 130 is, for example, an integrated circuit such as an ASIC and an FPGA, or an electronic circuit such as a CPU and an MPU.

In the first embodiment, the image processing apparatus 200 performs various processing on a CSF image group acquired by the MRI apparatus 100, to provide the operator with information for evaluating the dynamic state of the CSF. Specifically, the image processing apparatus 200 performs the following: "index derivation" to derive an index indicating the dynamic state of the CSF by analyzing the CSF image group; and "processing display" to display processed images obtained by assigning a color to the observation target region in the CSF images.

The details thereof will be described below. In the "index derivation", the image processing apparatus 200 derives velocity information of the CSF or the like, and causes a graph that indicates displacement of the CSF to be displayed, as an analysis result. In the "processing display", for example, the image processing apparatus 200 causes part of the CSF region designated as an observation target to be displayed in an emphasized manner with a red color, on the CSF image. The units included in the controlling circuitry 130 perform processing for the "index derivation" and the "processing display". The outline of the processing is briefly explained herein, and the details of the processing will be described later. Although the following embodiments illustrate the example where the image processing apparatus 200 performs both the "index derivation" and the "processing display", the embodiments are not limited thereto, but the image processing apparatus 200 may perform only one of them.

The observation target input receiving circuitry 231 receives an input of information to designate an observation target. For example, the observation target input receiving circuitry 231 receives an input of information designating an observation target region (anatomical region) by an operator's mouse operation or keyboard operation. For example, the designated information of the observation target information that is input is used for designating an analyzing method used in the "index derivation". For example, the observation target input receiving circuitry 231 also receives an input of information that designates an observation target region by an operator's mouse operation or keyboard operation. For example, the designated information of the observation target region that is input is used for designating a CSF region to which a color is assigned in the "processing display".

The CSF region extraction circuitry 232 extracts, from each of the CSF images included in the CSF group, CSF regions. Each of the CSF images includes: a region in which no CSF exists (hereinafter referred to as "non-CSF region"); and a region in which the CSF exists (hereinafter referred to as "CSF form region").

The CSF form region includes the following, by the spatial labeling inversion pulse (Time-SLIP) method described later: a tagged CSF region (hereinafter referred to as "tagged CSF region"); and a CSF region that is not tagged (hereinafter referred to as "non-tagged CSF region").

The CSF region extraction circuitry 232 extracts CSF form regions and tagged CSF regions from the respective CSF images, based on the designated information of the observation target area input by the observation target input receiving circuitry 231.

The index derivation circuitry 233 derives an index indicating a dynamic state of the CSF, by analyzing a CSF region group (such as a tagged CSF region group) extracted from each of the CSF images by the CSF region extraction circuitry 232. In the processing, the index derivation circuitry 233 performs analysis by an analyzing method associated with the observation target region, an input of which has been received by the observation target input receiving circuitry 231.

The processed image generating circuitry 234 generates a processed image obtained by processing the original CSF image, and causes the generated processed image to be displayed on the display 212. For example, the processed image generating circuitry 234 generates an image obtained by changing the color of the region designated as the observation target region on the original CSF image, as the processed image.

The display controlling circuitry 235 causes an analysis result display screen to be displayed on the display 212. For example, the display controlling circuitry 235 causes the processed image generated by the processed image generating circuitry 234 and a graph based on the index derived by the index derivation circuitry 233 to be displayed side by side on the display 212.

Figure 4A:
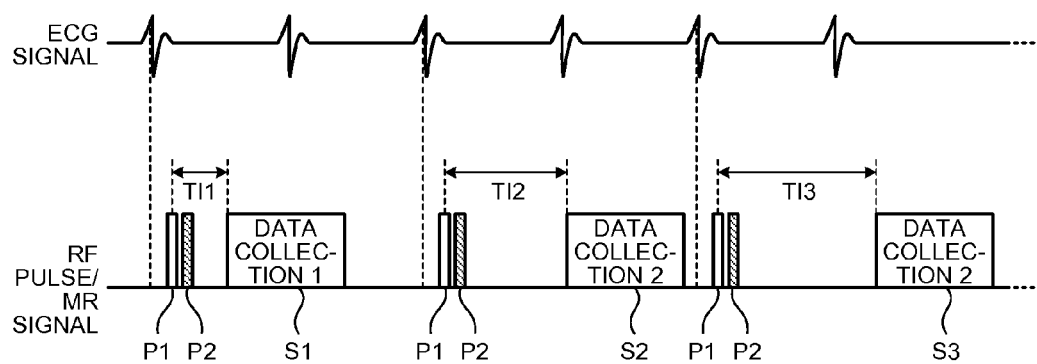
FIG. 4A and FIG. 4B are explanatory drawings of the Time-SLIP method in the first embodiment.
Figure 4B:
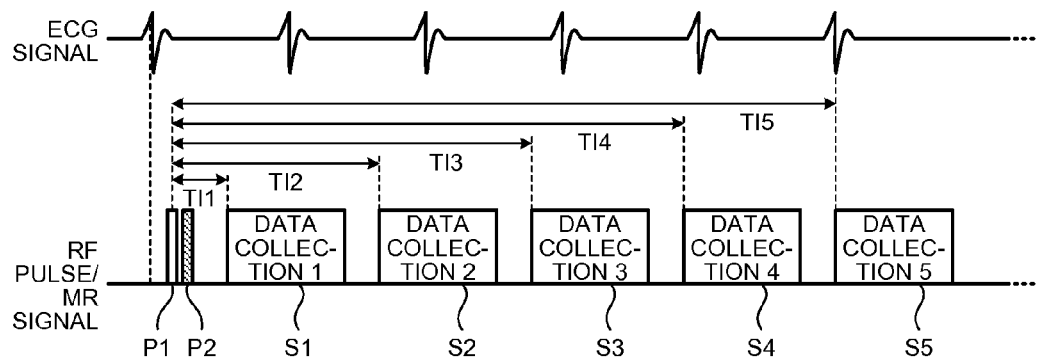

FIG. 4A and FIG. 4B are diagrams for explaining the Time-SLIP method in the first embodiment. In FIG. 4A and FIG. 4B, the horizontal axis indicates time. The Time-SLIP method is a method in which MR signals are collected after a predetermined time after the fluid is tagged by a tagging pulse, to relatively heighten or relatively lower the signal value of the fluid serving as an observation target, and thereby selectively draw and visualize the fluid.

In the Time-SLIP method, for example, an inversion recovery pulse (hereinafter referred to as "IR pulse") is applied as a tagging pulse, thereby tagging the fluid. Collection of MR signals is started after inversion time (TI) has been applied since a timing at which a tagging pulse is applied. Collection of these MR signals is performed by, for example, the steady state free precession (SSFP) or fast asymmetric spin echo or fast advanced spin echo (FASE). The TI is properly set according to the set positions of the imaging region and the tagged region, and the relaxation time of the longitudinal magnetization of the background tissue.

As illustrated in FIG. 4A and FIG. 4B, the tagging pulse includes a spatially non-selective IR pulse P1 and a spatially selective IR pulse P2, and both the pulses are applied almost simultaneously after a given time has passed since a trigger signal. The spatially non-selective IR pulse P1 is an IR pulse that is applied without selection of a region, and the spatially selective IR pulse P2 is an IR pulse that is applied to a tagged region. The spatially non-selective IR pulse P1 may be omitted. FIG. 4A and FIG. 4B illustrate the example of using an electrocardiogram (ECG) signal as a trigger signal, but the embodiments are not limited thereto. The trigger signal may be other biological signals such as a respiration signal and a pulse wave signal (peripheral pulse gating (PPG) signal), or any signal such as a clock signal of the MRI apparatus 100.

The imaging region and the tagged region are properly set according to the imaging purpose of the MR image. This embodiment illustrates an example (Example 1) where both the spatially non-selective IR pulse P1 and the spatially selective IR pulse P2 are applied, and an example (Example 2) where only the spatially selective IR pulse P2 is applied, on the assumption that a tagged region is set in an imaging region.

Example 1

The example illustrates the case of setting a tagged region in an imaging region, and applying both the spatially non-selective IR pulse P1 and the spatially selective IR pulse P2. First, the spatially non-selective IR pulse P1 is applied, and thereby the longitudinal magnetization of the whole imaging region is inverted to have a negative value, and thereafter gradually recovers. Thereafter, when the spatially selective IR pulse P2 is applied to the tagged region, only the longitudinal magnetization in the tagged region is inverted again to have a positive value. Thereafter, after the time TI has passed, suppose that MR signals are collected around a null point at which the absolute value of the longitudinal magnetization of the background tissue is zero. In such a case, the fluid flowing in the tagged region flows out of the tagged region. By contrast, the fluid that was flowing outside the tagged region flows into the tagged region. Because the fluid that was flowing in the tagged region has longitudinal magnetization of a positive value and the outside of the tagged region has longitudinal magnetization of substantially "zero", a significant contrast exists between them, and the fluid that has flown out of the tagged region is drawn brightly. In addition, because the fluid that was flowing outside the tagged region has longitudinal magnetization of substantially "zero" and the inside of the tagged region has longitudinal magnetization having a positive value, a significant contrast exists between them, and the fluid flowing into the tagged region is drawn darkly.

Example 2

The example illustrates the case of setting a tagged region in an imaging region, and applying only the spatially selective IR pulse P2. First, the spatially selective IR pulse P2 is applied to the tagged region, and thereby the longitudinal magnetization in the tagged region is inverted, thereby having a negative value, and thereafter gradually recovers. Thereafter, after the time TI has passed, suppose that MR signals are collected around a null point at which the absolute value of the longitudinal magnetization in the tagged region is zero. In such a case, the fluid flowing in the tagged region flows out of the tagged region. By contrast, the fluid that was flowing outside the tagged region flows into the tagged region. Because the fluid that was flowing in the tagged region has longitudinal magnetization of substantially "zero" and the outside of the tagged region has longitudinal magnetization of a positive value, a significant contrast exists between them, and the fluid that has flown out of the tagged region is drawn darkly. In addition, because the fluid that was flowing outside the tagged region has longitudinal magnetization of a positive value and the inside of the tagged region has longitudinal magnetization of substantially "zero", a significant contrast exists between them, and the fluid flowing into the tagged region is drawn brightly.

The embodiments are not limited to the examples above, but may be properly changed according to the imaging purpose or the like. For example, the tagging pulse is not limited to an IR pulse, but may be a saturation (SAT) pulse, a spatial modulation of magnetization (SPAMM) pulse, or a DANTE pulse. The setting positions of the imaging region and the tagged region may be changed as desired. For example, a tagged region may be set outside the imaging region. In addition, a plurality of tagged regions may be set. The spatially non-selective IR pulse P1 and the spatially selective IR pulse P2 may be applied a plurality of times.

In the first embodiment, the sequence controlling circuitry 120 acquires a CSF image group for a plurality of time phases by imaging, for the purpose of evaluating the dynamic state of the CSF. The following two methods may be used as the method. The pulse sequences illustrated in FIG. 4A and FIG. 4B are only examples, and the intervals of TI and the data collection time may be properly changed.

(First Method)

As illustrated in FIG. 4A, after time "TI1" has passed since application of a tagging pulse, the sequence controlling circuitry 120 collects MR signals of the imaging region for "one slice (or one slice encoding)". The sequence controlling circuitry 120 repeats 1 Repetition Time (TR) in which MR signals for "one slice (or one slice encoding)" are collected, while gradually increasing TI from "TI1", "TI2", "TI3", . . . . In this manner, the sequence controlling circuitry 120 acquires MR signals for a plurality of time phases, that is, a CSF image group for a plurality of frames arranged in a time series. Setting a number of small intervals of TI enables observation of the dynamic state of the CSF corresponding to more minute time change.

(Second Method)

As illustrated in FIG. 4B, the sequence controlling circuitry 120 applies a tagging pulse, and thereafter repeats data collection for "one slice (or one slice encoding)" sequentially a plurality of times. The successively collected MR signals have TI that gradually increases from "TI1", "TI2", "TI3", . . . . In this manner, the sequence controlling circuitry 120 acquires MR signals for a plurality of time phases after application of a tagging pulse once, that is, a CSF image group for a plurality of frames arranged in a time series. With the second method also, setting a number of small intervals of TI enables observation of the dynamic state of the CSF corresponding to more minute time change.

Figure 5:
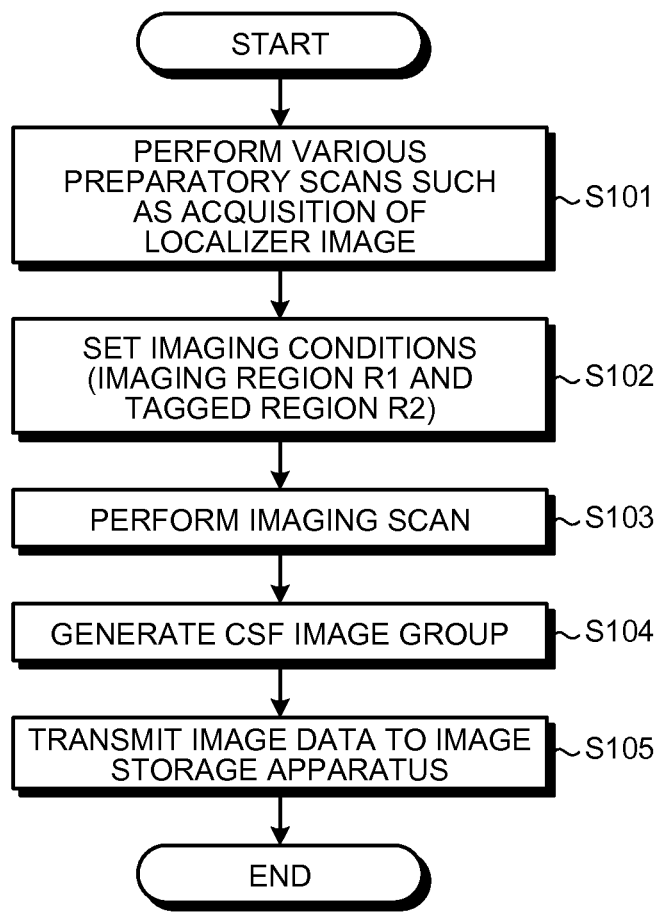
FIG. 5 is a flowchart illustrating processing procedures of the MRI apparatus in the first embodiment.

FIG. 5 is a flowchart illustrating processing procedures of the MRI apparatus 100 according to the first embodiment. Typically, before the processing illustrated in FIG. 5, the operator has already selected a series of protocols (such as a protocol for acquiring a localizer image, a protocol for imaging a sensitivity map, a protocol for shimming, and a protocol for imaging scan) to acquire a CSF image group at a plurality of time phases, on the GUI for inputting imaging conditions. The sequence controlling circuitry 120 performs various processing illustrated in FIG. 5, in accordance with the selected series of protocols.

As illustrated in FIG. 5, first, the sequence controlling circuitry 120 performs various preparatory scans such as localizer image acquisition, sensitivity map imaging, and shimming (Step S101). Thereafter, the imaging condition setting circuitry 133a causes the localizer image acquired in Step S101 to be displayed on the display 135, and receives setting of imaging conditions (such as setting of the imaging region R1 and the tagged region R2) from the operator (Step S102).

Figure 6:
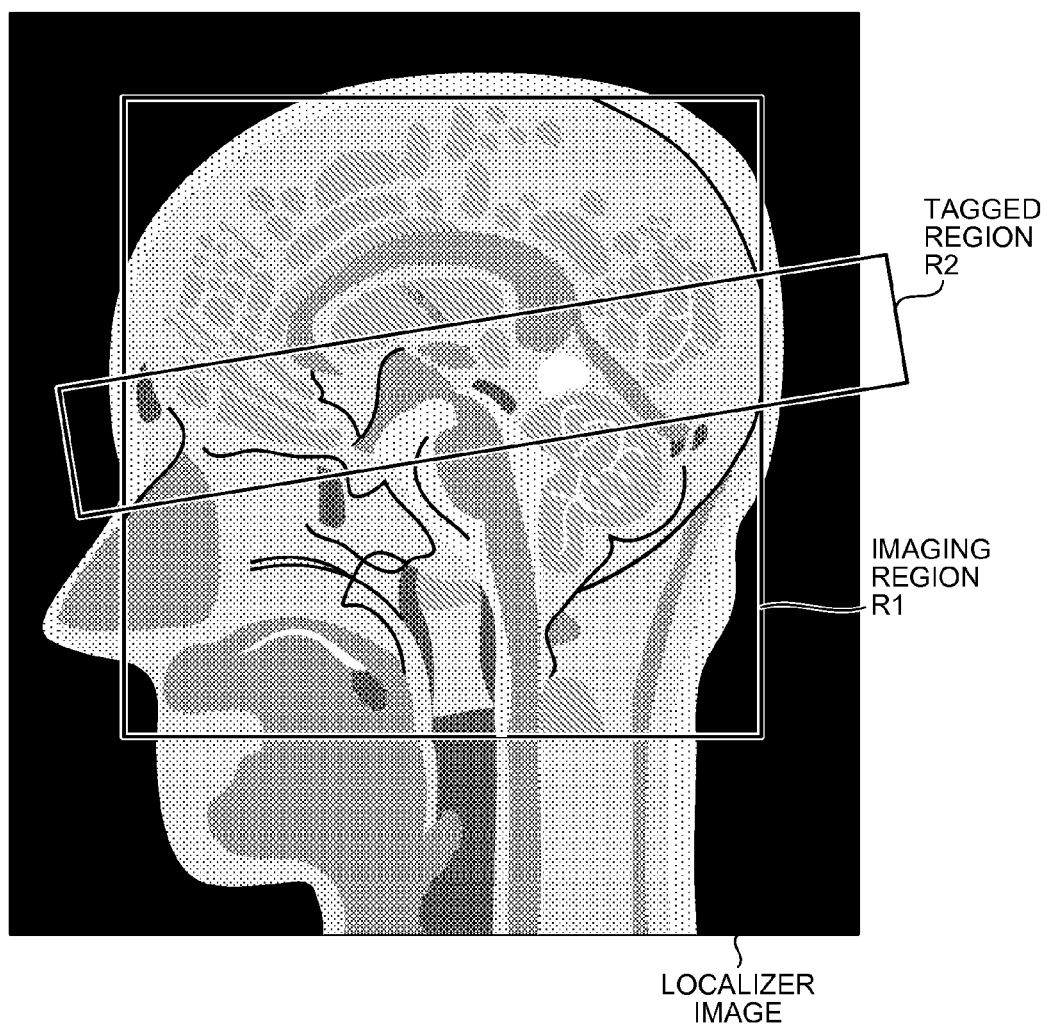
FIG. 6 is a diagram illustrating a localizer image in the first embodiment.
Figure 7:
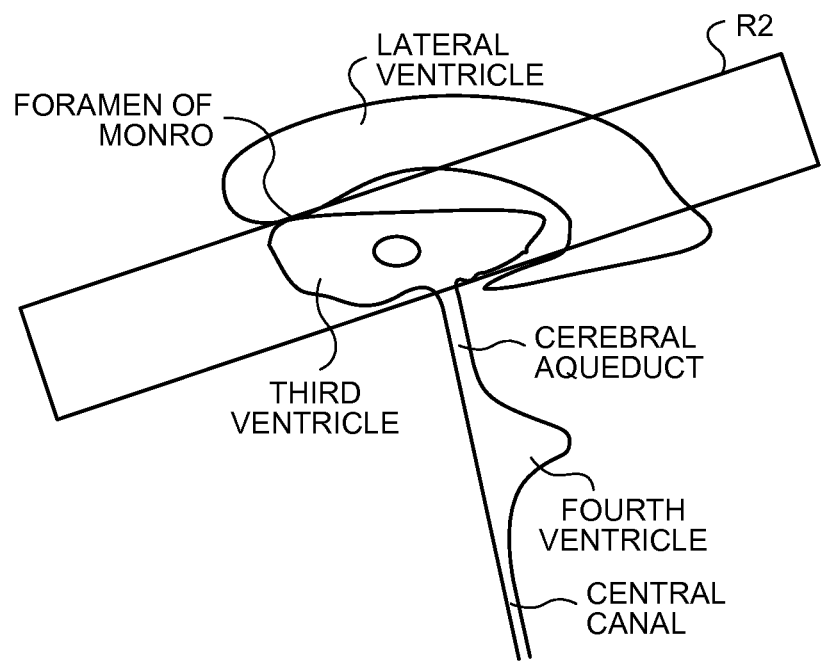
FIG. 7 is an explanatory drawing of setting a tagged region in the first embodiment.

FIG. 6 is a diagram illustrating the localizer image in the first embodiment, and FIG. 7 is a diagram for explaining setting of the tagged region R2 in the first embodiment. For example, as illustrated in FIG. 6, the imaging condition setting circuitry 133a causes an image of a plane (referred to as "arrow-shaped cross section" or "sagittal plane") that divides the brain into a left part and a right part to be displayed as the localizer image on the GUI, and receives setting of the imaging region R1 and the tagged region R2 from the operator on the GUI.

The first embodiment is aimed at evaluating the dynamic state of the CSF. CSF has no cardiac cycle unlike the blood, and its dynamic state of the fluid greatly changes at each timing of data collection. The dynamic state of such fluid is observed for various clinical purposes. For example, discrimination between hydrocephalus and non-hydrocephalus can be supported by detailed analysis of presence/absence of circulation of the fluid, presence/absence of traffic of fluid into a lumen that appears to be closed, or velocities of the fluid for the respective regions.

FIG. 7 illustrates an anatomical structure of the brain. In a normal brain, it is known that CSF moves to and fro, for example, between the third ventricle and the fourth ventricle. In addition, for example, the CSF traffics between the lateral ventricle and the third ventricle via the foramen of Monro. For example, the flow velocity of the CSF is comparatively high in the third ventricle and the fourth ventricle, while the flow velocity of the CSF is comparatively slow in the lateral ventricle. The flow velocity of the CSF thus differs between the regions. By contrast, in the brain suffering from hydrocephalus, the dynamic state different from that in the normal brain is observed. For example, the traffic of the CSF is lost between the lateral ventricle and the third ventricle, or the flow velocities in the respective regions change.

For this reason, in the first embodiment, the imaging region R1 and the tagged region R2 are set such that the CSF can be viewed along the moving direction or the diffusion direction of the CSF. In the example illustrated in FIG. 6 and FIG. 7, for example, the imaging region R1 is set to include all of the lateral ventricle, the foramen of Monro, the third ventricle, the cerebral aqueduct, the fourth ventricle, and the central canal, and the tagged region R2 is set on the third ventricle serving as the starting point out of which the CSF flows in the imaging region R1. As a result, the obtained CSF image enables viewing of the CSF that moves to and fro between the third ventricle and the fourth ventricle via the cerebral aqueduct.

The imaging region R1 is not necessarily set to include all of the lateral ventricle, the foramen of Monro, the third ventricle, the cerebral aqueduct, the fourth ventricle, and the central canal. For example, the imaging region R1 may be set to include only the lateral ventricle, only the third ventricle, only the cerebral aqueduct, or only the fourth ventricle. In addition, the tagged region R2 is not necessarily set on the third ventricle. For example, the tagged region R2 may be set on the lateral ventricle, the cerebral aqueduct, or the fourth ventricle. As described above, the imaging region R1 and the tagged region R2 may be set to enable viewing of the CSF along the moving direction or the diffusion direction of the CSF. So as to include which region among characteristic regions in the brain the imaging region R1 and the tagged region R2 are set may be changed as desired according to the purpose of imaging.

With reference to FIG. 5 again, when setting of the imaging conditions is finished as described above, the sequence controlling circuitry 120 performs imaging scan, to acquire MR signals corresponding to a CSF image group at a plurality of time phases (Step S103). When the imaging scan is performed and MR signals are acquired, the image generating circuitry 136 generates a CSF image group for a plurality of time phases based on the acquired MR signals (Step S104). Thereafter, the MRI apparatus 100 transmits image data of a CSF image group for a plurality of time phases to the image storage apparatus 300, and stores the image data therein (Step S105).

Figure 8:
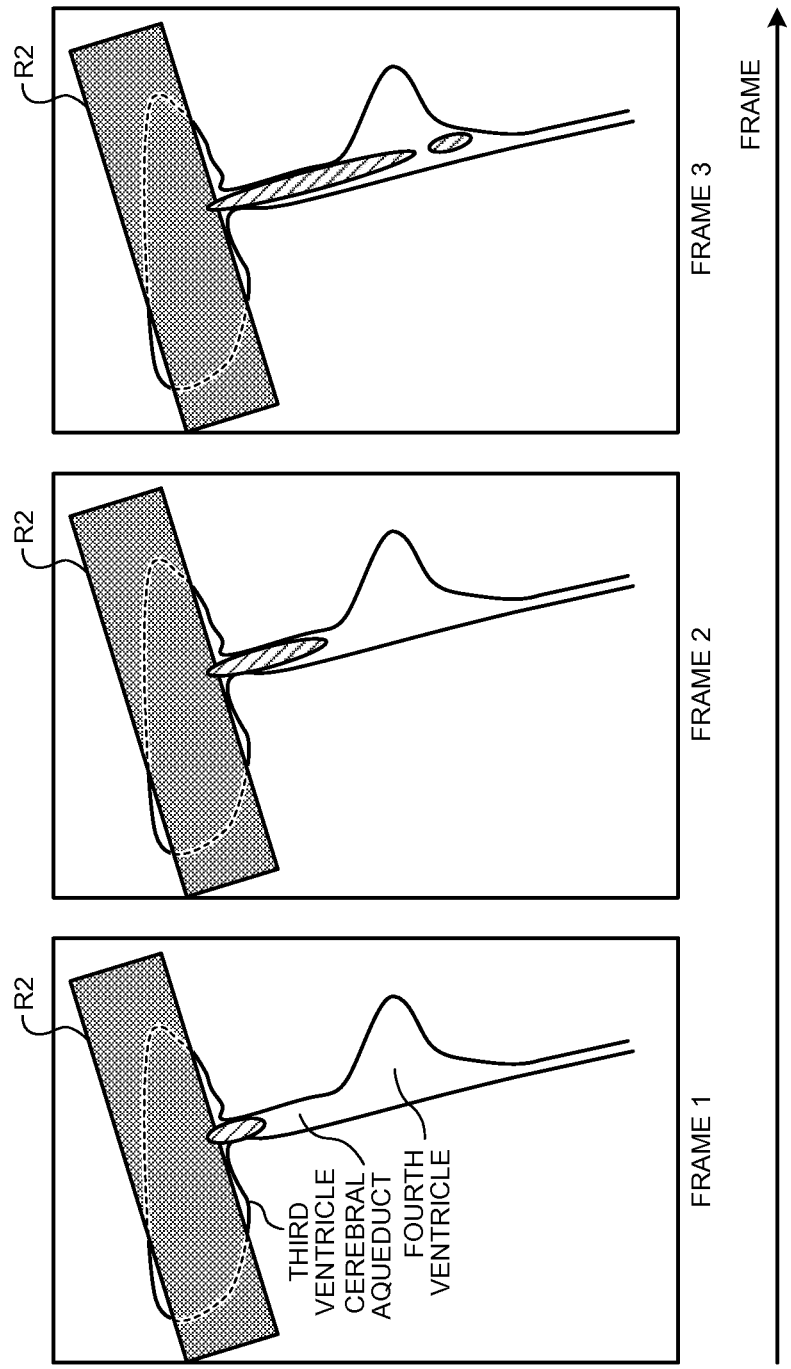
FIG. 8 is a diagram illustrating an example of a CSF image group at a plurality of time phases in the first embodiment.

FIG. 8 is a diagram illustrating an example of a CSF image group for a plurality of time phases in the first embodiment. In FIG. 8, Frame 1, Frame 2, Frame 3, . . . , are a group of a series of CSF images (enlarged views of a part) for a plurality of time phases that are obtained by reconstructing MR signals acquired in different TIs, as illustrated in FIG. 4A and FIG. 4B. As illustrated in FIG. 8, the CSF images are arranged in time series according to the time, the imaging timing, or the frame number. The CSF images illustrated in FIG. 8 illustrate the state where the CSF tagged in the tagged region R2 flows out of the third ventricle to the cerebral aqueduct, and from the cerebral aqueduct to the fourth ventricle.

The following is an explanation of processing performed by the image processing apparatus 200. The image processing apparatus 200 performs processing on the CSF image group for a plurality of time phases acquired by the MRI apparatus 100. The image processing apparatus 200 causes to display an index obtained by analyzing the CSF image group ("index derivation"), and causes to display a processed image obtained by performing image processing on the CSF image group ("processing display"), thereby providing the operator with information for evaluating the dynamic state of the CSF.

The method for analyzing the CSF image group performed in the "index derivation" should be properly selected according to the evaluation purpose of the analysis, and the type of the dynamic state of the CSF to be analyzed for the evaluation purpose. The following explanation illustrates two analyzing methods as examples for convenience' sake, but the embodiments are not limited thereto. For example, although the following explanation illustrates an example of deriving indexes related to three positions as Analyzing Method 2, the method is also a mere example. For example, the method is not limited to the structure of deriving indexes related to three positions, but can be changed as desired, for example, to derive indexes related to two positions or four positions.

(Analyzing Method 1)

Analyzing Method 1 is a method of tracking temporal displacement of a position in a region of the fluid, thereby deriving an index indicating the dynamic state of the fluid for the position. For example, suppose that analysis is performed for the purpose of evaluating the presence/absence of the traffic and the flow velocity of the CSF in the cerebral aqueduct. In such a case, for example, the image processing apparatus 200 extracts a tagged CSF region flowing out of the third ventricle to the fourth ventricle from each of the CSF images. The image processing apparatus 200 designates a forefront position of a distal end of the extracted tagged CSF region, and derives an index indicating the flow velocity for the designated position.

(Analyzing Method 2)

Analyzing Method 2 is a method of tracking temporal displacement of a plurality of positions in a region of the fluid, thereby deriving an index (or indexes) indicating the dynamic state of the fluid for each of the plurality of positions. For example, suppose that analysis is performed for the purpose of evaluating the presence/absence of the traffic and the flow velocity of the CSF in the prepontine cistern. In such a case, for example, the image processing apparatus 200 extracts, from each of the CSF images, a tagged CSF region flowing out in the two directions of the upper and lower directions. The image processing apparatus 200 designates positions of both ends of the extracted tagged CSF region, and derives indexes indicating the flow velocity for the respective three positions, that is, the designated both ends and the midpoint therebetween.

As described above, the subsequent processing in the image processing apparatus 200 (for example, whether analysis is performed by Analyzing Method 1 of deriving an index indicating the flow velocity or Analyzing Method 2 of deriving three indexes) differs according to the purpose of the evaluation. For this reason, the image processing apparatus 200 according to the first embodiment receives an input of an analysis target region from the operator in advance, to designate the analyzing method in the index derivation circuitry 233.

Figure 9:
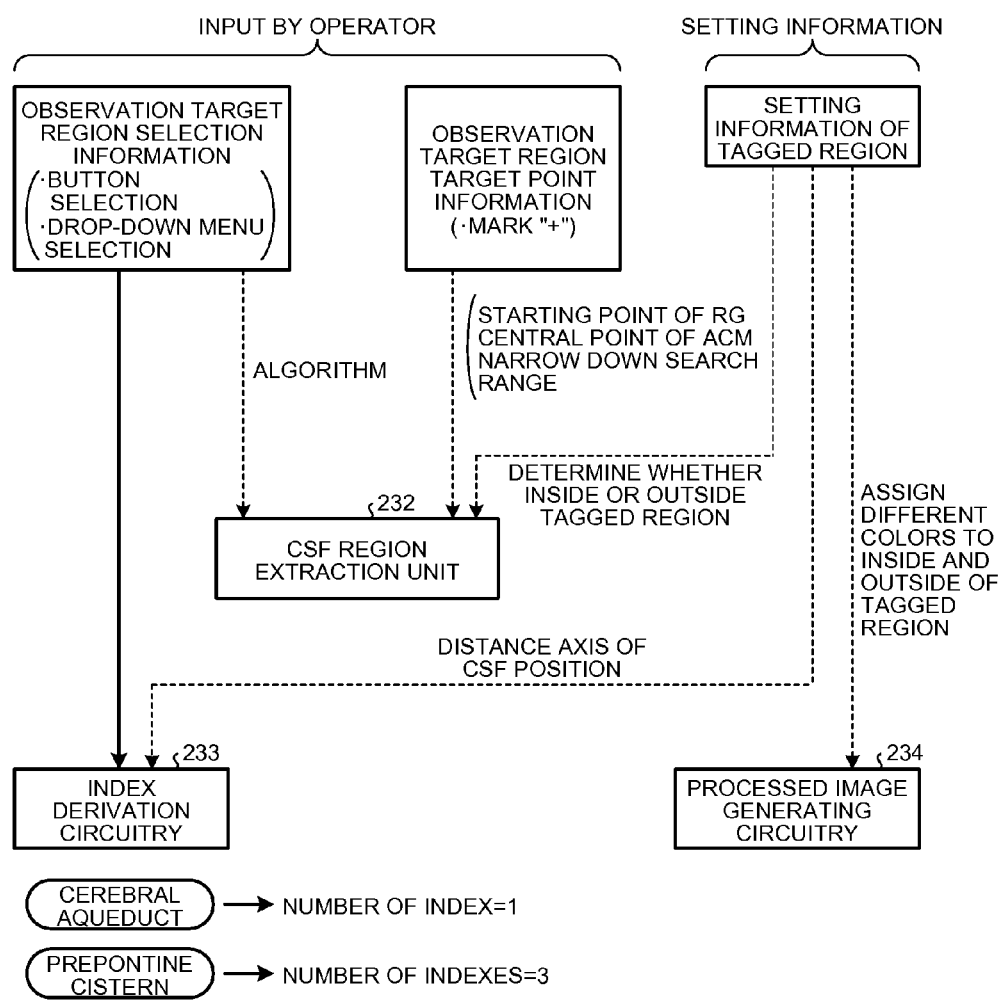
FIG. 9 is a diagram illustrating relation between input information of the image processing apparatus and processing at the subsequent stage in the first embodiment.

FIG. 9 is a diagram illustrating relation between input information and the subsequent processing of the image processing apparatus 200 according to the first embodiment. For example, in the first embodiment, the observation target input receiving circuitry 231 receives an input of "observation target region selection information" (hereinafter referred to as "region selection information") from the operator, as illustrated in FIG. 9. For example, the observation target input receiving circuitry 231 receives designation of "cerebral aqueduct" or "prepontine cistern" as the observation target region in the form of button selection or drop-down menu selection. The forms such as button selection and drop-down menu selection are mere examples.

The association of the observation target region with the analyzing method is known by advance association. For example, the index derivation circuitry 233 maintains association, by advance association, to perform analysis by the Analyzing Method 1 (the number of index is 1) when the "cerebral aqueduct" is designated as the observation target region, and perform analysis by the Analyzing Method 2 (the number of indexes is 3) when the "prepontine cistern" is designated as the observation target region.

For this reason, the index derivation circuitry 233 properly selects the analyzing method according to the observation target region designated by the operator, and performs analysis in accordance with the selected analyzing method. For example, when the "cerebral aqueduct" is designated as the observation target region, the index derivation circuitry 233 designates a position of a distal end of the tagged CSF region extracted from the CSF image, and derives an index indicating the flow velocity for the position of the distal end. In addition, for example, when the "prepontine cistern" is designated as the observation target region, the index derivation circuitry 233 designates positions of both ends of the tagged CSF region extracted from the CSF image, and derives indexes indicating the flow velocity for the respective positions of both ends and the midpoint therebetween.

The following explanation illustrates the example in which the index derivation circuitry 233 properly selects the analyzing method according to the observation target region designated by the operator to perform analysis in accordance with the selected analyzing method, but the embodiments are not limited thereto. For example, analysis by various analyzing methods may be performed in advance. In such a case, for example, when the display controlling circuitry 235 outputs analysis results, the index derivation circuitry 233 may refer to the observation target region designated by the operator, and select and output an analysis result obtained by the analyzing method corresponding to the observation target region.

In the meantime, as illustrated in FIG. 9, the "region selection information" may be used for not only designation of the analyzing method, but also processing performed by the CSF region extraction circuitry 232. In the first embodiment, the observation target input receiving circuitry 231 also receives an input of "observation target region target point information" (hereinafter referred to as "target point information") from the operator. The target point information may also be used for processing performed by the CSF region extraction circuitry 232. In the first embodiment, the image processing apparatus 200 receives setting information of the tagged region R2 as supplementary information attached to image data of the CSF image group. The setting information of the tagged region R2 may also be used for processing performed by the CSF region extraction circuitry 232, the index derivation circuitry 233, or the processed image generating circuitry 234. When the setting information of the tagged region R2 is not provided as supplementary information, for example, setting information of the tagged region R2 may be extracted by performing image processing on a CSF image of a frame having a small degree of relaxation (for example, a frame with the smallest TI) of the tagged region R2.

What information in the "region selection information", "target point information", and "setting information of the tagged region R2" is used for what processing and how the information is used depend on the subsequent processing performed by the unit and the algorithm used by the unit. Each of the information may be useful for the subsequent processing, or may not be useful. In addition, each of the information may be indispensable or may be substituted by another method. For this reason, for example, the operator is not ultimately required to input both the "region selection information" and "target point information", but the operator may input necessary information according to the circumstances. The relations between each of the information and the subsequent processing mentioned in the explanation of the processing performed by the units are mere examples.

Figure 10:
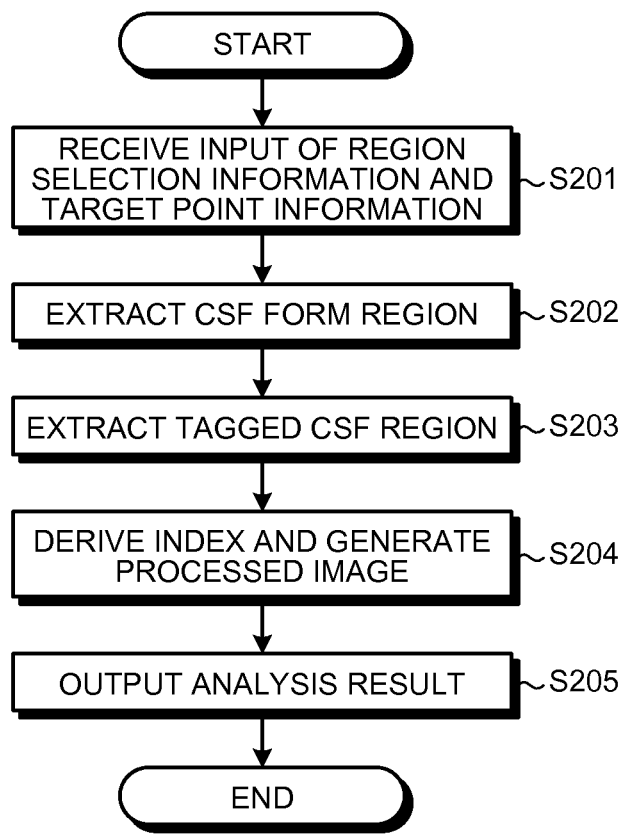
FIG. 10 is a flowchart illustrating processing procedures of the image processing apparatus in the first embodiment.

FIG. 10 is a flowchart illustrating processing procedures of the image processing apparatus 200 according to the first embodiment. FIG. 10 is based on the assumption that the image processing apparatus 200 has acquired image data of a CSF image group for a plurality of time phases from the MRI apparatus 100 or the image storage apparatus 300, or via a storage medium, and stored the image data in the CSF image group storage 221.

First, the observation target input receiving circuitry 231 causes the GUI for receiving input of the "region selection information" and "target point information" to be displayed on the display 212, and receives input of the "region selection information" and "target point information" from the operator (Step S201).

Figures 11, 12:
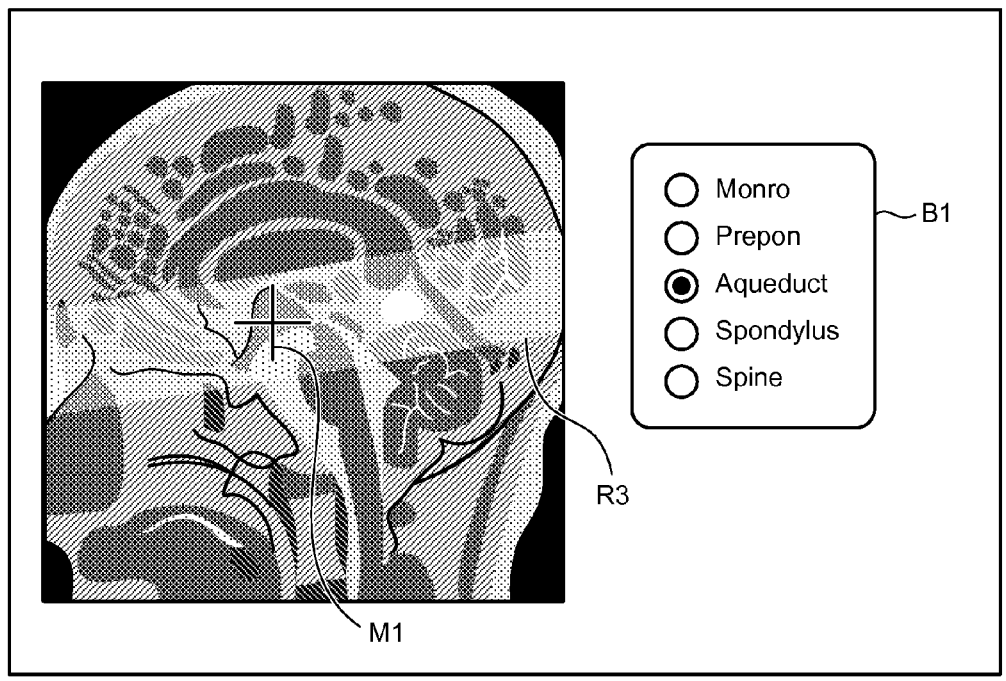
FIG. 11 is an explanatory drawing of an input receipt of observation target region selection information in the first embodiment.
FIG. 12 is an explanatory drawing of an input receipt of observation target region selection information in another embodiment.

FIG. 11 is a diagram for explaining an input receipt of region selection information in the first embodiment. For example, as illustrated in FIG. 11, the observation target input receiving circuitry 231 causes display of the GUI including the CSF image for receiving an input of the "target point information" and a button B1 for receiving an input of the "region selection information".

The observation target input receiving circuitry 231 typically uses a frame having the smallest TI among the frames for a plurality of time phases, as the CSF image for receiving an input of the "target point information". Because the longitudinal magnetization in the imaging region R1 or the tagged region R2 is not relaxed in a frame with a small TI, a contrast difference exists between the imaging region R1 and the tagged region R2. This helps the operator input the "target point information" while the operator recognizes the position of the tagged region R2. The frame illustrated in FIG. 11 also visualizes a tagged region R3 by contrast difference.

The CSF image for receiving an input of the "target point information" is not limited to a frame having the smallest TI. The observation target input receiving circuitry 231 may designate a frame having the largest contrast difference between the imaging region R1 and the tagged region R2 among the frames for a plurality of time phases, and use the designated frame as the CSF image for receiving an input of the "target point information".

By contrast, for example, the observation target input receiving circuitry 231 may use a frame in which the longitudinal magnetization in the imaging region R1 or the tagged region R2 is relaxed and a contrast difference between the imaging region R1 and the tagged region R2 is reduced, as the CSF image for receiving an input of the "target point information". For example, the observation target input receiving circuitry 231 may use a frame having the largest TI among the frames for a plurality of time phases. In such a case, the observation target input receiving circuitry 231 may cause the position of the tagged region R2 to be displayed on the CSF image, if necessary, using the "setting information of the tagged region R2".

As another example, the observation target input receiving circuitry 231 may analyze the CSF image group in the time direction, calculate a characteristic amount such as dispersion of the signal intensity, the maximum value, and signal transition, for each of the pixels, thereby employing a processed image obtained by some processing as the CSF image for receiving an input of the "target point information".

The observation target input receiving circuitry 231 also receives, for example, an input of a mark M1 of the sign "+" that indicates the target point, as the "target point information" on the CSF image displayed to receive an input of the "target point information". The observation target input receiving circuitry 231 notifies the CSF region extraction circuitry 232 of coordinate information of the position where the mark M1 is input.

The example of FIG. 11 illustrates the method of receiving an input of mark M1 of the sign "+" from the operator on the CSF image, but the embodiments are not limited thereto. The sign used as the mark M1 may be changed as desired. For example, the observation target input receiving circuitry 231 may prepare in advance a plurality of candidates for coordinate information serving as the target point by a machine learning algorithm, and cause the prepared candidates to be displayed on the GUI for the operator to select one therefrom.

The observation target input receiving circuitry 231 also causes the button B1 to be displayed for the operator to select one region name from a list of anatomical region names, as the GUI for receiving an input of the "region selection information". For example, the observation target input receiving circuitry 231 causes the button B1 to be displayed for selecting one region name in the names "Monro", "Prepon", "Aqueduct", "Spondylus", and "Spine". The name "Monro" corresponds to the "foramen of Monro", the name "Prepon" corresponds to the "prepontine cistern", the name "Aqueduct" corresponds to the "cerebral aqueduct", and the names "Spondylus" and "Spine" correspond to the "spine". For example, when the operator presses down the button "Aqueduct", the observation target input receiving circuitry 231 receives "cerebral aqueduct" as the "region selection information", and notifies the index derivation circuitry 233 of the information.

Figure 13:
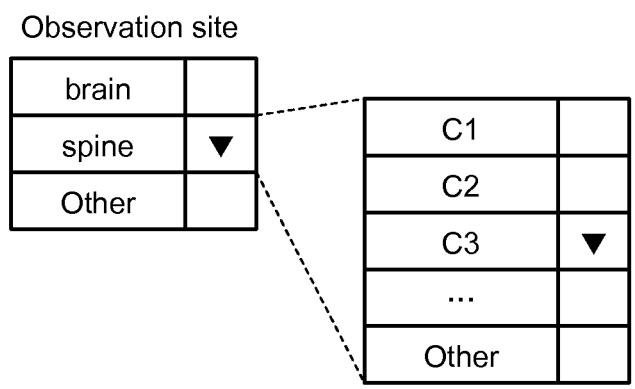
FIG. 13 is an explanatory drawing of an input receipt of observation target region selection information in another embodiment.

FIG. 11 illustrates the example of displaying the button B1 as the GUI for receiving an input of the "region selection information", but the embodiments are not limited thereto. FIG. 12 and FIG. 13 are diagrams for explaining an input receipt of the observation target region selection information in other embodiments. For example, as illustrated in FIG. 12 and FIG. 13, the observation target input receiving circuitry 231 may provide a GUI for receiving an input of the "region selection information" in the form of a drop-down menu. For example, the observation target input receiving circuitry 231 may provide a GUI in the form of a drop-down menu having a hierarchical structure to cause selection of a specific region after selection of a large classification, as illustrated in FIG. 13. The display "Observation site" indicates "type of the observation target region". The black triangle mark indicates the item that is selected. The observation target input receiving circuitry 231 may cause the operator to directly input the region name, instead of the form of causing the operator to select a region.

In addition, FIG. 11 illustrates the example of receiving inputs of both the "region selection information" and "target point information", but the embodiments are not limited thereto. For example, input of "target point information" may be omitted. In such a case, for example, the observation target input receiving circuitry 231 performs image processing on the CSF image using the input "region selection information", thereby extracting the form of the corresponding region from the CSF image. The observation target input receiving circuitry 231 automatically determines coordinate information serving as the target point by a machine learning algorithm, in accordance with the form of the extracted region. Examples of the machine learning algorithm in this case are a boosting method using a number of weak identification devices in combination, and a random tree method using a number of decision trees learned by training data obtained by random sampling.

With reference to FIG. 10 again, thereafter, the CSF region extraction circuitry 232 reads a CSF image group for a plurality of time phases from the CSF image group storage 221, and first of all extracts a CSF form region from each of the CSF images included in the CSF image group (Step S202). The CSF form region is a region in which a CSF simply exists, regardless of presence/absence of tagging. Thereafter, the CSF region extraction circuitry 232 extracts tagged CSF regions from the respective CSF form regions (Step S203).

The following is an explanation of an example of two-stage extraction processing performed by the CSF region extraction circuitry 232. The CSF region extraction circuitry 232 performs processing of extracting a CSF form region and processing of extracting a tagged CSF region on each of the CSF images included in the CSF image group. For example, the CSF region extraction circuitry 232 determines whether a pixel in the CSF image is a pixel in the tagged region R2 or a pixel outside the tagged region R2, for each of pixels in the CSF image, based on "the setting information in the tagged region R2".

For example, the CSF region extraction circuitry 232 also analyzes the CSF image group over a plurality of time phases with respect to a pixel determined to be located in the tagged region R2, to calculate the maximum value of the signal value at the plurality of time phases.

In addition, for example, the CSF region extraction circuitry 232 also analyzes the CSF image group over a plurality of time phases with respect to a pixel determined to be located outside the tagged region R2, to calculate a value that quantitatively indicates how the signal value of the pixel transitions with lapse of time. For example, the CSF region extraction circuitry 232 calculates dispersion. Large dispersion means the situation in which the signal value frequently repeats a high state and a low state, and means that the region is probably a region in which the tagged CSF moves to and fro. Specifically, the CSF likeliness increases as dispersion increases.

In addition, for example, the CSF region extraction circuitry 232 analyzes the CSF image group over a plurality of time phases with respect to a pixel determined to be located outside the tagged region R2, to calculate the degree of coincidence that indicates a degree of coincidence as to whether the pixel is CSF, by following Equation (1).

$$T_p = \sum_{f=1}^{F} t_p(f) \tag{1}$$

$$t_p(f) = \begin{cases} 1, & \text{if } f < f_n \text{ and } S_{f,p} < S_{f-1,p} \\ 1, & \text{if } f > f_n \text{ and } S_{f,p} > S_{f-1,p} \\ 0, & \text{else} \end{cases}$$

As described above, for example, the longitudinal magnetization of the CSF (non-tagged CSF) that received only application of the spatially non-selective IR pulse P1 outside the tagged region R2 has an inverted negative value, and thereafter gradually recovers. The process of recovery thereof includes a null point at which the absolute value of the longitudinal magnetization is zero. In Equation (1) above, "p" represents a pixel, and "f" represents a frame. The frame $f_n$ is a frame having the smallest absolute value of the longitudinal magnetization. The value "$t_p(f)$" is "1" when the signal value of its frame is smaller than the signal value of the previous frame, with respect to frames prior to the frame $f_n$ in the time direction. The value "$t_p(f)$" is "1" when the signal value of its frame is larger than the signal value of the previous frame, with respect to frames after the frame $f_n$ in the time direction. The value "$t_p(f)$" is "0" when the conditions above are not satisfied. The degree of coincidence "$T_p$" of each pixel is a value obtained by integrating "$t_p(f)$" in the time direction, and the larger the degree of coincidence "$T_p$", the higher CSF likeliness.

For example, the CSF region extraction circuitry 232 calculates a CSF likelihood of each pixel by Equation (2).

$$L_p = \alpha_p S_{m,p} + (1-\alpha_p)(\beta S_{v,p} + (1-\beta)T_p) \tag{2}$$

A pixel that is located in the tagged region R2 satisfies "$\alpha_p=1$". In such a case, only the first term on the right side of Equation (2) is reflected on calculation of the CSF likelihood. On the other hand, in the case of a pixel outside the tagged region R2, "$\alpha_p=0$" holds. In such a case, only the second term on the right side of Equation (2) is reflected on calculation of the CSF likelihood. The part "$S_{m,p}$" in the first term is the maximum value of the signal value determined for a pixel in the tagged region R2. The part "$S_{m,p}$" in the second term is dispersion calculated for a pixel outside the tagged region R2. The part "$T_p$" in the second term is a degree of coincidence calculated for a pixel outside the tagged region R2. The weighting coefficient "$\beta$" of a linear sum of the dispersion and the coincidence is properly set. The CSF likelihood calculated by Equation (2) indicates that the larger the CSF likelihood is, the higher CSF likeliness of the pixel becomes.

For example, the CSF region extraction circuitry 232 performs, for example, threshold processing on the CSF likelihood calculated by Equation (2), thereby extracting the CSF form region from the CSF image.

In the processing, CSF form regions may be scattered in slightly distant positions. For this reason, the CSF region extraction circuitry 232 further performs image processing such as region growing (RG) on the designated CSF form regions. The CSF region extraction circuitry 232 may use "target point information" (see FIG. 9), such as performing region growing by using the position that is input as the "target point information", as the starting point.

Thereafter, the CSF region extraction circuitry 232 extracts a tagged CSF region from the CSF form regions. As described above, a significant contrast difference should occur between the tagged CSF and non-tagged CSF, in a certain range around a null point of the CSF. For this reason, for example, the CSF region extraction circuitry 232 performs, for example, threshold processing based on a difference in signal value on the CSF form regions, to perform segmentation between a tagged CSF region and a non-tagged CSF region, thereby extracting a tagged CSF region. For example, the CSF region extraction circuitry 232 also performs, for example, clustering processing by k-means or discriminant analysis method on the CSF form regions, thereby extracting a tagged CSF region.

The two-stage extraction processing above is a mere example. For example, the CSF region extraction circuitry 232 may use active counter model (ACM) or active shape model (ASM) for extracting CSF form regions. The CSF region extraction circuitry 232 can use the "target point information" (see FIG. 9), such as performing search by ACM and ASM with the position that is input as the "target point information" used as the central point.

For example, the CSF region extraction circuitry 232 can use the "region selection information" (see FIG. 9) for selecting the algorithm for extracting the CSF form regions. For example, the CSF region extraction circuitry 232 uses a model of ACM or ASM corresponding to the region designated by the "region selection information". For example, the CSF region extraction circuitry 232 can also use "region selection information" for performing template matching or pattern recognition to narrow down a search range for CSF form regions from the CSF image (see FIG. 9). For example, the CSF region extraction circuitry 232 performs template matching and pattern recognition using a template or a pattern corresponding to the region designated by the "region selection information". For example, the CSF region extraction circuitry 232 can also use the "target point information" for performing template matching or pattern recognition with the range narrowed down to a range around the position that is input as the "target point information". Such narrowing enables processing at higher speed, and enables highly accurate identification, because parts other than the designated region and portions around the designated target point can be removed from the processing target.

With reference to FIG. 10 again, in Step S203, when a tagged CSF region is extracted from each of the CSF images included in the CSF image group, the index derivation circuitry 233 analyzes the tagged CSF regions, to derive indexes indicating the dynamic state of the CSF (Step S204). The processed image generating circuitry 234 generates a processed image in which colors are assigned to the tagged CSF region and the non-tagged CSF region (Step S204).

First, the processing performed by the index derivation circuitry 233 will be explained hereinafter. As explained with reference to FIG. 9, the index derivation circuitry 233 properly selects the analyzing method in accordance with the "region selection information", an input of which has been received by the observation target input receiving circuitry 231, and performs analysis according to the selected analyzing method.

For example, when the "region selection information" is "cerebral aqueduct", the index derivation circuitry 233 selects Analyzing Method 1 (the number of index is 1), to derive an index. For example, when the "region selection information" is "prepontine cistern", the index derivation circuitry 233 selects Analyzing Method 2 (the number of indexes is 3), to derive indexes.

Figure 14A:
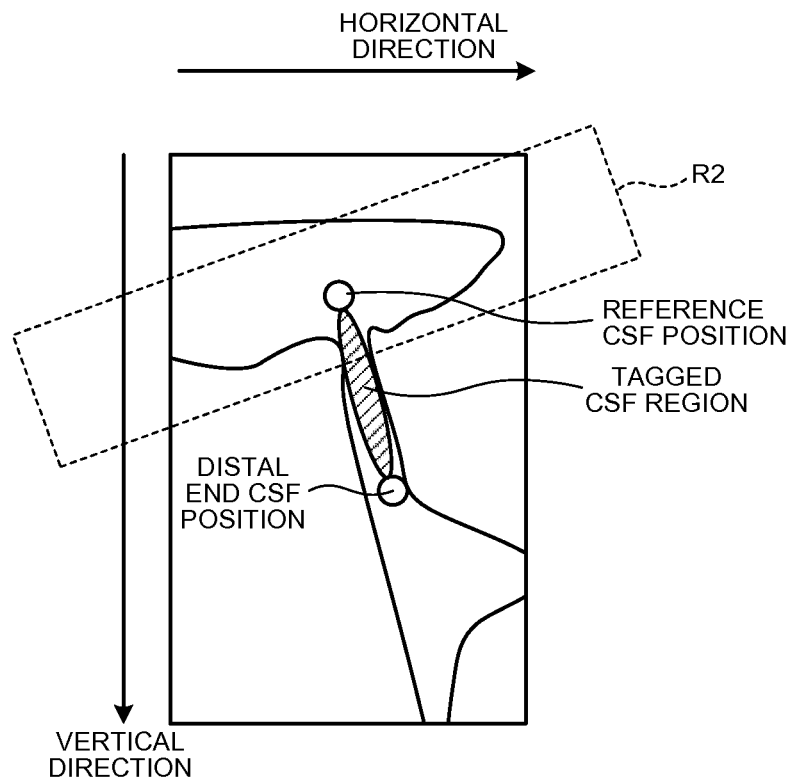
FIG. 14A and FIG. 14B are explanatory drawings of index derivation by Analyzing Method 1 in the first embodiment.
Figure 14B:
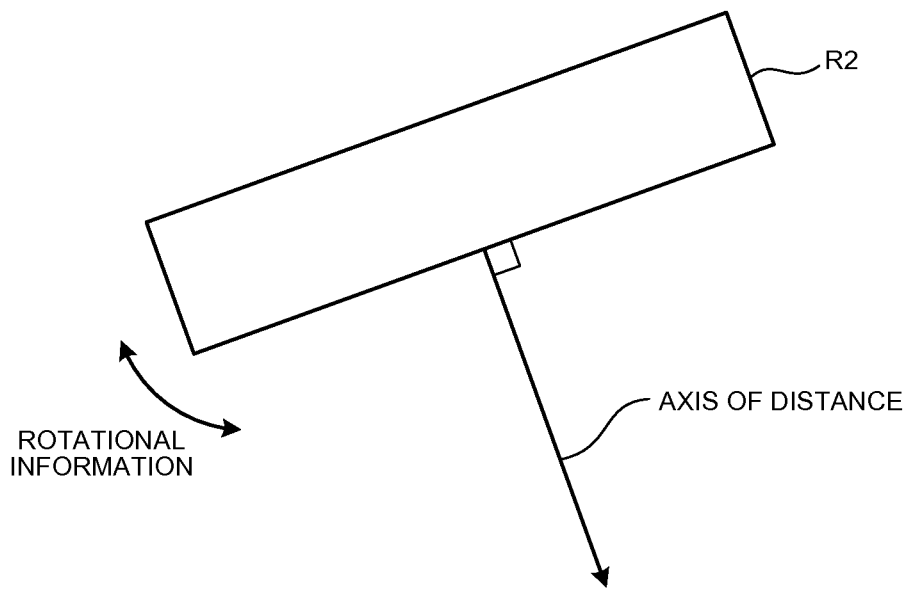

FIG. 14 is a diagram for explaining index derivation by Analyzing Method 1 according to the first embodiment. FIG. 14 illustrates an enlarged view of part of a CSF image at a time phase. When Analyzing Method 1 (the number of index is 1) is selected, the index derivation circuitry 233 designates a position having the minimum coordinates in the horizontal direction and the vertical direction in the tagged CSF region extracted from the CSF image, as "reference CSF position". The index derivation circuitry 233 also designates a position having the largest distance from the "reference CSF position" in the tagged CSF region, as "distal end CSF position". For example, when the axis of distance is set, the index derivation circuitry 233 can use the "setting information of the tagged region R2" (see FIG. 9). For example, the index derivation circuitry 233 can determine the distance from the tagged region R2 using an axis in a direction of perpendicular line that perpendicularly extends from the rectangular tagged region R2. In the determination, the index derivation circuitry 233 uses rotational information that indicates the orientation of the tagged region R2.

The index derivation circuitry 233 determines coordinates of the "distal end CSF position" for the respective CSF images included in the CSF image group, and outputs the coordinates of the "distal end CSF position" displaced with lapse of time, as indexes indicating the dynamic state of the CSF. The index derivation circuitry 233 can also determine the time between frames from the frame rate, to determine an average velocity in a plurality of frames based on the velocity between frames and the regression line, from the moving amount of the CSF per unit time. Output of such indexes allows the operator to properly evaluate the presence/absence of traffic of the CSF and the flow velocity thereof in the cerebral aqueduct.

Figure 15:
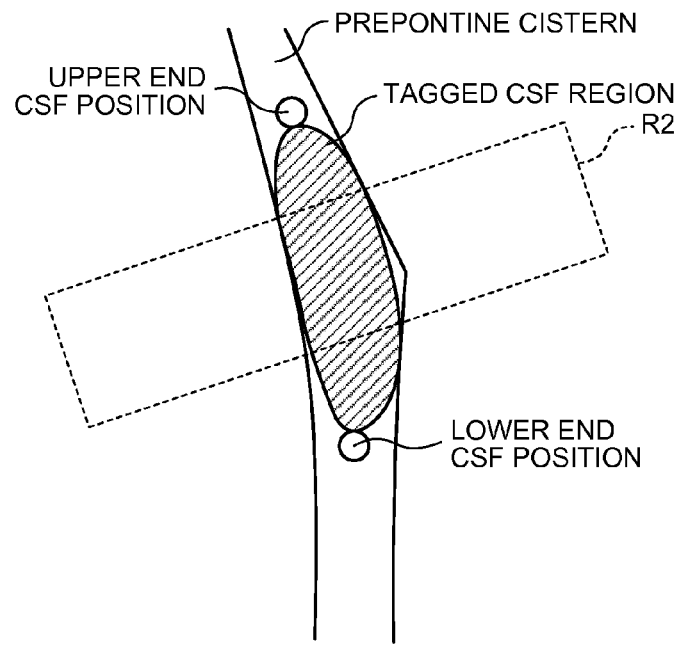
FIG. 15 is an explanatory drawing of index derivation by Analyzing Method 2 in the first embodiment.

FIG. 15 is a diagram for explaining index derivation by Analyzing Method 2 in the first embodiment. FIG. 15 illustrates an enlarged view of part of a CSF image at a time phase. FIG. 15 also illustrates the case where the tagged region R2 is set in substantially the center of the prepontine cistern. When Analyzing Method 2 (the number of indexes is 3) is selected, the index derivation circuitry 233 designates a position having the minimum coordinates in the horizontal direction and the vertical direction in the tagged CSF region extracted from the CSF image, as "upper end CSF position". The index derivation circuitry 233 also designates a position having the maximum coordinates in the horizontal direction and the vertical direction in the tagged CSF region extracted from the CSF image, as "lower end CSF position". The index derivation circuitry 233 also designates "midpoint" between the "upper end CSF position" and the "lower end CSF position".

The index derivation circuitry 233 also determines coordinates of the "upper end CSF position", the "lower end CSF position", and the "midpoint" for each of the CSF images included in the CSF image group, and outputs the coordinates of these CSF positions displaced with lapse of time, as indexes indicating the dynamic state of the CSF. The index derivation circuitry 233 also determines moving amounts from the reference CSF position (for example, the midpoint in the frame of the first time phase) for the respective "upper end CSF position", the "lower end CSF position", and the "midpoint", and outputs the moving amounts as indexes indicating the dynamic state of the CSF. Output of such indexes allows the operator to properly evaluate the presence/absence of traffic of the CSF and the flow velocity thereof in the prepontine cistern.

The indexes derived by the index derivation circuitry 233 are not limited to the examples above. For example, the index derivation circuitry 233 may use the area of the tagged CSF region, as an index indicating the dynamic state of the CSF. The index derivation circuitry 233 calculates the area of the tagged CSF region for each frame with the unit of the number of pixels or square meter, to derive expansion of the CSF region per unit time or the dispersion velocity.

As other examples, the index derivation circuitry 233 can properly use the following indexes: (a) total variation norm or an average value of total variation norm of the CSF position corresponding to the collection time of the CSF image; (b) dispersion in time direction of the CSF position corresponding to the collection time of the CSF image; (c) slope of the regression line plotting, against time, the area of the tagged CSF region corresponding to the collection time of the CSF image; (d) total variation norm or an average value of total variation norm of the area of the tagged CSF region corresponding to the collection time of the CSF image; (e) dispersion in time direction of the area of the tagged CSF region corresponding to the collection time of the CSF image; and (f) a moving amount of the CSF position corresponding to the collection time of a plurality of CSF images, and a unit moving amount normalized by the collection time.

The following is an explanation of processing performed by the processed image generating circuitry 234. For example, the processed image generating circuitry 234 directly process the original CSF image, thereby generating a processed image obtained by assigning colors to the tagged CSF region and non-tagged CSF region. For example, when the original CSF image is a gray-scale image and RGB values of all the pixels are "gray", the processed image generating circuitry 234 changes the RGB values, to display the pixels corresponding to the tagged CSF region extracted by the CSF region extraction circuitry 232 in "red". For example, the processed image generating circuitry 234 also changes the RGB values, to display the pixels corresponding to the "distal end CSF position" designated by the index derivation circuitry 233 in "green".

The generation examples of the processed image described above are mere examples. For example, the processed image generating circuitry 234 may generate a processed image by generating a superimposing image in which colors are assigned, and superimposing the superimposing image on the original CSF image, instead of directly processing the original CSF image. Although the example above illustrates the case of assigning "red" to the tagged CSF region and assigning "green" to the distal end CSF position, the observation target regions to which colors are assigned and the colors to be assigned can be changed as desired. For example, when the colors to be assigned are changed according to the inside/outside of the tagged region R2, the processed image generating circuitry 234 can use the "setting information of the tagged region R2" (see FIG. 9).

With reference to FIG. 10 again, the display controlling circuitry 235 generates an analysis result display screen using the indexes derived by the index derivation circuitry 233 and the processed image generated by the processed image generating circuitry 234, and causes the generated analysis result display screen to be displayed on the display 212 (Step S205).

In the first embodiment, the display controlling circuitry 235 designates the analyzing method based on the "region selection information", an input of which has been received by the observation target input receiving circuitry 231, and further provides an analysis result display screen according to the designated analyzing method. The association between the analyzing method and the analysis result display screen according to the analyzing method is known in advance by association conducted in advance.

For example, when a graph is generated from the indexes derived by the index derivation circuitry 233, the display controlling circuitry 235 prepares a graph according to the analyzing method. For example, when the analyzing method designated from the "region selection information" is Analyzing Method 1, for example, the display controlling circuitry 235 plots coordinates of the "distal end CSF position", and generates a graph showing a regression line thereof. For example, when the analyzing method designated from the "region selection information" is Analyzing Method 2, for example, the display controlling circuitry 235 plots coordinates of the "upper end CSF position", "lower end CSF position", and "midpoint", and generating a graph showing respective regression lines thereof.

In addition, for example, when the display controlling circuitry 235 displays the processed image generated by the processed image generating circuitry 234, the display controlling circuitry 235 displays supplementary information according to the analyzing method in a superimposed manner. For example, when the analyzing method designated from the "region selection information" is Analyzing Method 1, for example, the display controlling circuitry 235 causes marks that indicate the "reference CSF position" and "distal end CSF position" to be displayed in a superimposed manner on the processed image, and causes an arrow that connects the "reference CSF position" with the "distal end CSF position" to be displayed in a superimposed manner thereon. For example, when the analyzing method designated from the "region selection information" is Analyzing Method 2, for example, the display controlling circuitry 235 causes marks that indicate the "upper end CSF position", "lower end CSF position", and "midpoint" to be displayed in a superimposed manner on the processed image, and causes a bar that indicates the length of the distance connecting the "upper end CSF position" with the "lower end CSF position" to be displayed thereon side by side as supplementary information.

The first embodiment illustrates the example where the display controlling circuitry 235 performs generation of a graph and displays supplementary information in a superimposed manner, but the embodiments are not limited thereto. For example, the index derivation circuitry 233 may perform processing up to generation of a graph according to the analyzing method. In addition, for example, the processed image generating circuitry 234 may perform processing up to displaying supplementary information in a superimposed manner on the processed image according to the analyzing method. In such a case, the display controlling circuitry 235 may simply controls to display the graph generated by the index derivation circuitry 233 and the processed image generated by the processed image generating circuitry 234 side by side, as the analysis result display screen. The display controlling circuitry 235 also properly performs other display controls, such as synchronization of the processed image and the graph.

Figure 16:
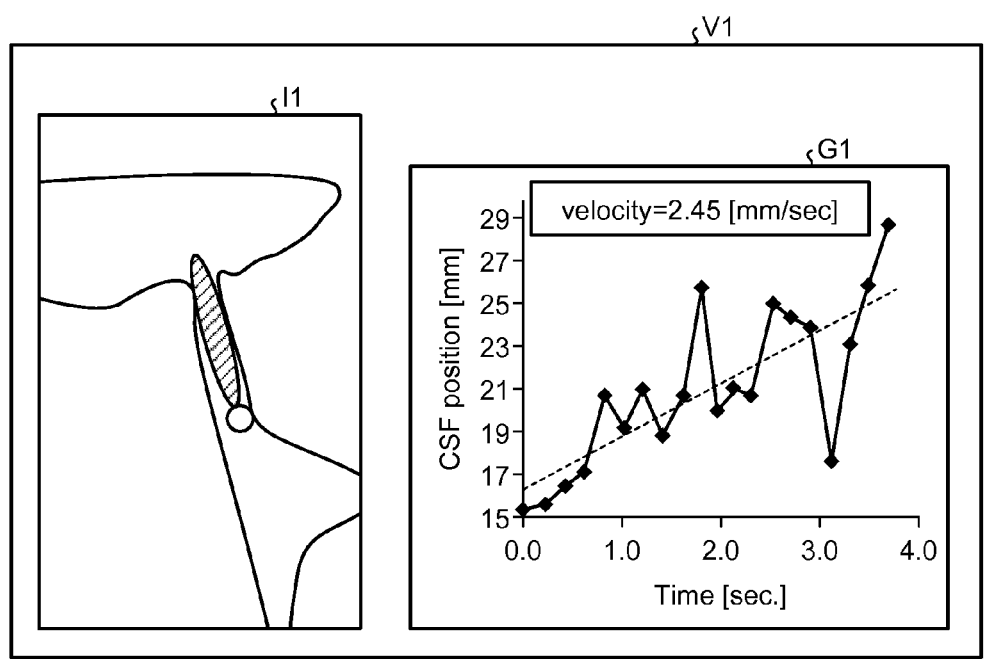
FIG. 16, FIG. 17 and FIG. 18 are explanatory drawings of an analysis result display screen in the first embodiment.
Figure 17:
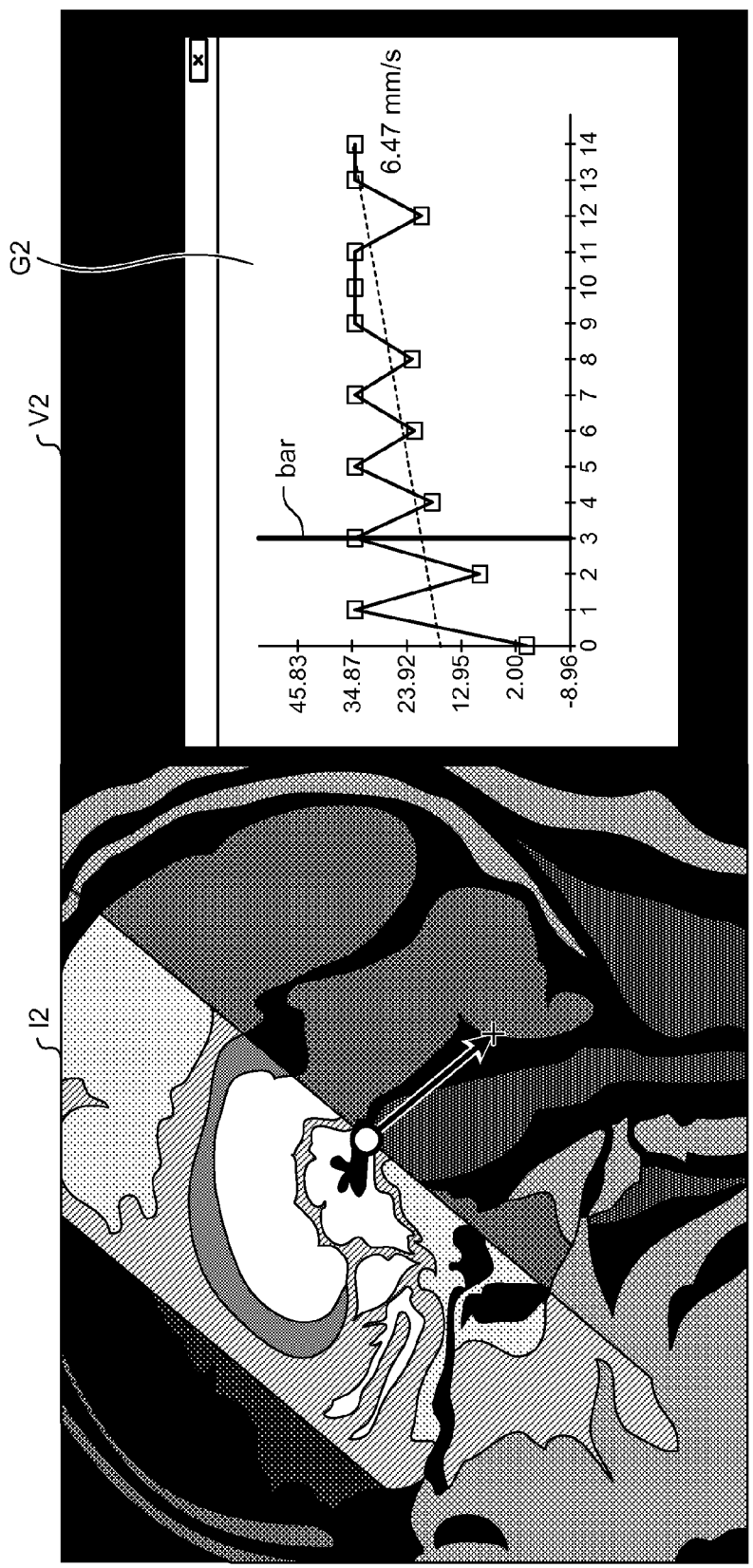
Figure 18:
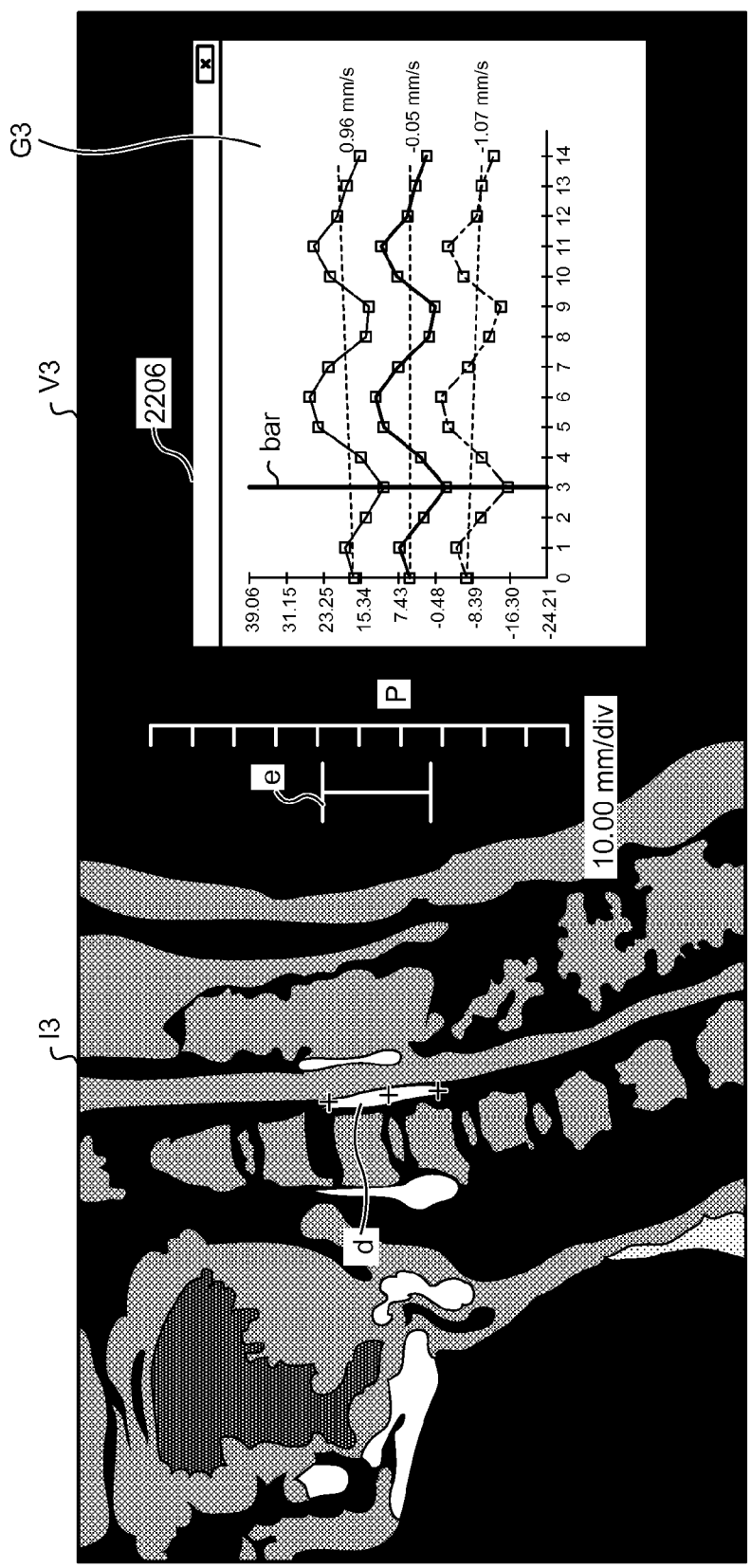

FIG. 16 to FIG. 18 are diagrams for explaining analysis result display screens according to the first embodiment. FIG. 16 and FIG. 17 correspond to the case where the CSF image group is analyzed by Analyzing Method 1, and FIG. 18 corresponds to the case where the CSF image group is analyzed by Analyzing Method 2.

FIG. 16 will be explained hereinafter. FIG. 16 illustrates an analysis result display screen V1. The analysis result display screen V1 displays, for example, a processed image I1 and a graph G1 generated by the display controlling circuitry 235 side by side. The processed image I1 visualizes, for example, a tagged CSF region to which the color "red" is assigned, and a distal end CSF position to which the color "green" is assigned. The processed image I1 may be continuously displayed over a plurality of time phases as if it were a moving image.

In the graph G1, the horizontal axis is the elapsed time, and the vertical axis is the CSF position. For example, when the "region selection information", an input of which has been received by the observation target input receiving circuitry 231 is "cerebral aqueduct", the display controlling circuitry 235 designates that analysis has been performed by Analyzing Method 1. Thereafter, as display control corresponding to Analyzing Method 1, the display controlling circuitry 235 generates a graph G1 obtained by plotting the "distal end CSF positions" for the respective frames derived by the index derivation circuitry 233, draws the regression line thereof (illustrated by a dotted line in FIG. 16) on the graph G1, and further displays average velocity information (velocity) corresponding to the slope of the regression line.

By observing the analysis result display screen V1, the operator can easily recognize the distal end CSF positions for the respective frames and average velocity information of a plurality of frames, and properly evaluate the dynamic state of the CSF for each of the frames and the dynamic state of the CSF serving as an average of a plurality of frames. The analysis result display screen V1 in FIG. 16 illustrates, together with specific numerical value information, the dynamic state of the CSF that does not always continue to move in a certain direction but moves as a whole in a direction of gradually going away from the reference CSF position, while moving to and fro in the direction of going away from the reference CSF position and in the direction of approaching the reference CSF direction.

FIG. 17 will be explained hereinafter. FIG. 17 illustrates an analysis result display screen V2. The analysis result display screen V2 displays, for example, a processed image I2 and a graph G2 generated by the display controlling circuitry 235 side by side. For example, when the "region selection information", an input of which has been received by the observation target input receiving circuitry 231 is "cerebral aqueduct", the display controlling circuitry 235 designates that analysis has been performed by Analyzing Method 1. Thereafter, as display control corresponding to Analyzing Method 1, the display controlling circuitry 235 causes marks that indicate the "reference CSF position" (mark ○) and "distal end CSF position" (mark x) to be displayed in a superimposed manner, and causes an arrow that connects the marks to be displayed in a superimposed manner thereon, as illustrated in FIG. 17. When the processed images are continuously displayed over a plurality of time phases, the display controlling circuitry 235 may control to display the arrow in a switched manner in response to switching to the processed image of the next time phase. This display mode is used when the flow of the CSF in one direction is observed, like the "cerebral aqueduct" and "foramen of Monro".

The display controlling circuitry 235 further generates the graph G2 obtained by plotting the "distal end CSF positions" for the respective frames derived by the index derivation circuitry 233, draws the regression line thereof (illustrated by a dotted line in FIG. 17) on the graph G2, and further controls to display average velocity information corresponding to the slope of the regression line. FIG. 17 also displays a bar that clearly illustrates the corresponding frame on the graph G2 in synchronization with continuous display of the processed images I2.

FIG. 18 is now explained. FIG. 18 illustrates an analysis result display screen V3. The analysis result display screen V3 displays, for example, a processed image I3 and a graph G3 generated by the display controlling circuitry 235 side by side. For example, when the "region selection information", an input of which has been received by the observation target input receiving circuitry 231 is "prepontine cistern", the display controlling circuitry 235 designates that analysis has been performed by Analyzing Method 2. Thereafter, as display control corresponding to Analyzing Method 2, the display controlling circuitry 235 controls to display the processed image I3 and the graph G3 as illustrated in FIG. 18 side by side. This display mode is used when the flow of the CSF moving in the vertical direction is observed, like the "prepontine cistern".

For example, the display controlling circuitry 235 causes marks (+ mark) that indicate the "upper end CSF position", "lower end CSF position", and "midpoint" of a tagged CSF region to be displayed in a superimposed manner on the processed image I3. For example, the display controlling circuitry 235 also controls to display a bar e that indicates the length of the distance connecting the "upper end CSF position" and "lower end CSF position" side by side as supplementary information.

The display controlling circuitry 235 further generates the graph G3 obtained by plotting the "upper end CSF positions", "lower end CSF positions", and "midpoints" for the respective frames derived by the index derivation circuitry 233, draws the respective regression lines thereof (illustrated by dotted lines in FIG. 18) on the graph G3, and further controls to display average velocity information corresponding to the slopes of the regression lines for the respective CSF positions. FIG. 18 also displays a bar that clearly illustrates the corresponding frame on the graph G3 in synchronization with continuous display of the processed images I3.

The display controlling circuitry 235 may perform a series of processing from the input reception processing performed by the observation target input receiving circuitry 231 successively with the analysis result display screens illustrated in FIG. 16 to FIG. 18. Specifically, at the stage before analysis, the display controlling circuitry 235 controls to display, for example, the CSF image for inputting "target point information", instead of a processed image, in the analysis result display screens illustrated in FIG. 16 to FIG. 18, and does not display a graph. Here, for example, when the operator inputs "region selection information" in the form of drop-down menu selection and further inputs "target point information", the processing is started by the CSF region extraction circuitry 232, the index derivation circuitry 233, and the processed image generating circuitry 234. At the stage after analysis, the display controlling circuitry 235 replaces the CSF image for inputting "target point information" by a processed image, causes supplementary information according to the analyzing method to be displayed in a superimposed manner, and generates a graph to display the graph side by side.

Effects of First Embodiment

As described above, the first embodiment enables proper provision of information for evaluating the dynamic state of the CSF. Specifically, in the first embodiment, the image processing apparatus 200 provides the operator with the GUI that receives designation of the observation target region and the observation target region that the operator wishes to observe. In addition, when the image processing apparatus 200 receives designation of the observation target region and the observation target region on the GUI from the operator, the image processing apparatus 200 uses these pieces of designation information for the subsequent processing. For example, the image processing apparatus 200 performs analysis by the analyzing method according to the observation target region designated by the operator, and derives proper indexes. In addition, for example, the image processing apparatus 200 generates a processed image such that the observation target region designated by the operator is displayed in an emphasized state. As described above, the image processing apparatus 200 discriminates an observation point desired by the operator, and adaptively switches the analyzing method and the display method. This structure enables flow analysis and display of the CSF by the observation method and with the observation target region intended by the operator.

Second Embodiment

The first embodiment illustrates the method of receiving an input of the mark M1 of sign "+" on the CSF image, as the target point information that indicates the analysis target region. In addition, the coordinate information of the input target point is used as the starting point of region growing, the central point of search by ACM and ASM, and for narrowing down the search range of template matching and pattern recognition, in the subsequent CSF region extraction processing. However, the embodiments are not limited thereto.

For example, the units that perform the subsequent processing can obtain supplementary information from input of the target point information, by determining in advance the meaning based on the positional relation between the target point information and the tagged region R2, the meaning in the case where the target point information is subjected to moving operation, and the meaning in the case where target point information is input for one path in a branching path. The following explanation illustrates the case where the processed image generating circuitry 234 uses the target point information, but the embodiments are not limited thereto. For example, the CSF region extraction circuitry 232 can perform extraction processing by a method suitable for extracting the analysis target region designated by the target point information. For example, the index derivation circuitry 233 can derive indexes for the analysis target region designated by the target point information.

FIG. 19 to FIG. 28 are diagrams for explaining input of target point information according to another embodiment. FIG. 19 to FIG. 28 illustrate the prepontine cistern as an example of the observation target region, but the embodiments are not limited thereto, but may be applied to other observation target regions in the same manner. In each of FIG. 19 to FIG. 28, (A) is a diagram for explaining an input of the observation target region, and (B) is a diagram illustrating a processed image generated by the processed image generating circuitry 234 in accordance with an input of the observation target region. (B) illustrates the difference between assigned colors by difference in pattern, for the sake of convenience of the explanation.

Figure 19A:
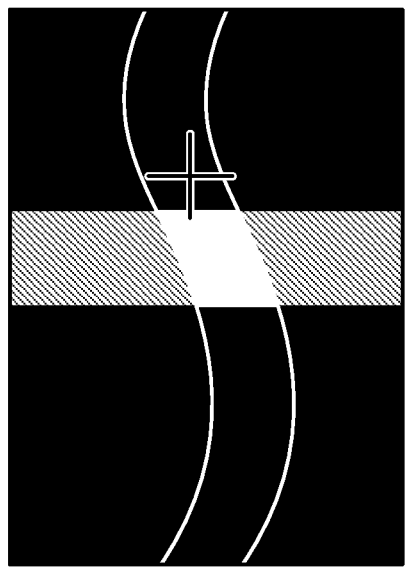
FIG. 19A and FIG. 19B are explanatory drawings of input of target point information in a second embodiment.

FIG. 19A illustrates an example where the observation target input receiving circuitry 231 receives an input of the mark M1 outside the tagged region R2. For example, it is determined in advance that a region of a CSF that flows from the side where the target point information is input into the tagged region R2 should be designated as the CSF region serving as the observation target, when target point information is input outside the tagged region R2.

Figure 19B:
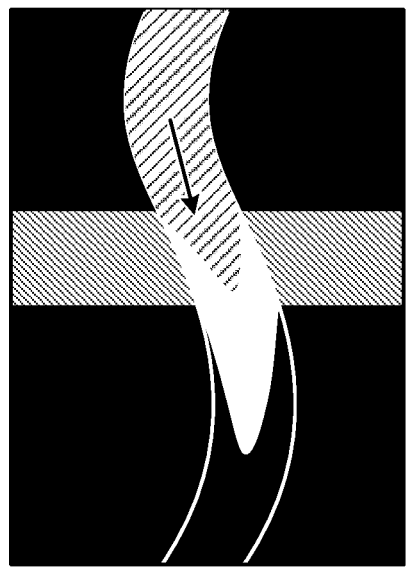

For example, the processed image generating circuitry 234 is notified of the input information received by the observation target input receiving circuitry 231. The processed image generating circuitry 234 designates the region that flows into the tagged region R2 from the upper side thereof and excludes the tagged CSF region, among the CSF form regions extracted by the CSF region extraction circuitry 232. Thereafter, the processed image generating circuitry 234 generates a processed image to display the designated region in "red", for example, as illustrated in FIG. 19B.

Figure 20A:
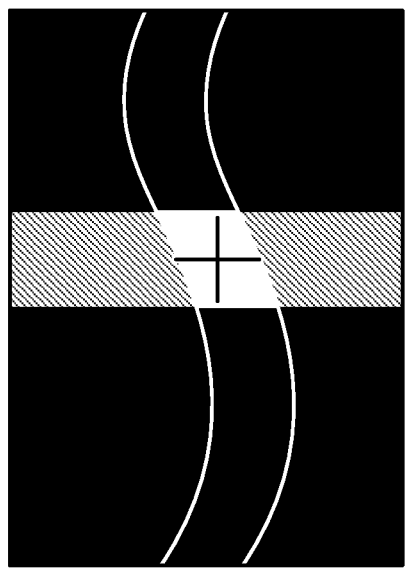
FIG. 20A, FIG. 20B, FIG. 21A, FIG. 21B, FIG. 22A, FIG. 22B, FIG. 23A, FIG. 23B, FIG. 24A, FIG. 24B, FIG. 25A, FIG. 25B, FIG. 26A, FIG. 26B, FIG. 27A, FIG. 27B, FIG. 28A and FIG. 28B are explanatory drawings of input of target point information in the second embodiment.

FIG. 20A illustrates an example where the observation target input receiving circuitry 231 receives an input of the mark M1 inside the tagged region R2. For example, it is determined in advance that a region of a CSF that flows out of the tagged region R2 should be designated as the CSF region serving as the observation target, when target point information is input inside the tagged region R2.

Figure 20B:
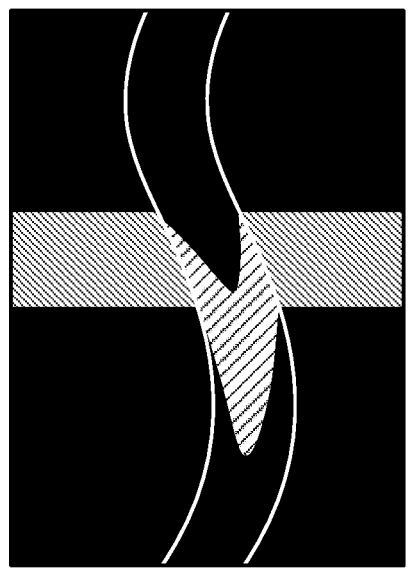

For example, the processed image generating circuitry 234 is notified of the input information received by the observation target input receiving circuitry 231. The processed image generating circuitry 234 generates a processed image to display the tagged CSF region extracted by the CSF region extraction circuitry 232 in "red", for example, as illustrated in FIG. 20B.

Figure 21A:
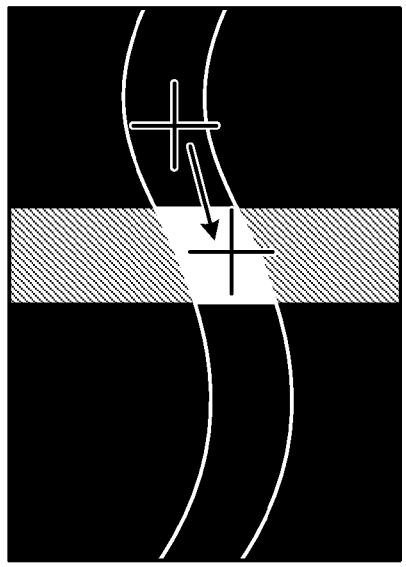

FIG. 21A illustrates an example where the position of the mark M1, an input of which has been received outside the tagged region R2, has been transitioned to the inside of the tagged region R2 due to a moving operation by the operator. The observation target input receiving circuitry 231 receives that the position of the mark M1 once received outside the tagged region R2 has been transitioned to the inside of the tagged region R2 thereafter. In such a case, it is determined in advance that a region of a CSF that flows from the outside into the inside of the tagged region R2 should be designated as the CSF region serving as the observation target, in the same manner as the track of movement of the mark M1.

Figure 21B:
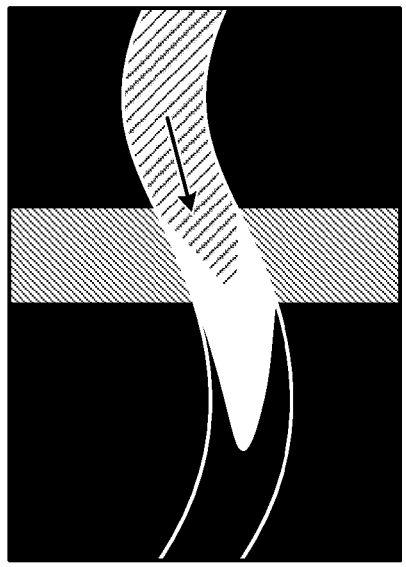

For example, the processed image generating circuitry 234 is notified of the input information received by the observation target input receiving circuitry 231. The processed image generating circuitry 234 designates the region that flows into the tagged region R2 from the upper side thereof and excludes the tagged CSF region, among the CSF form regions extracted by the CSF region extraction circuitry 232. Thereafter, the processed image generating circuitry 234 generates a processed image to display the designated region in "red", for example, as illustrated in FIG. 21B.

Figure 22A:
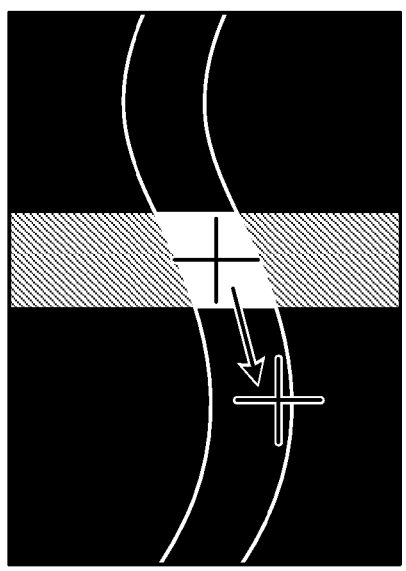

FIG. 22A illustrates an example where the mark M1, an input of which has been received inside the tagged region R2, has been moved to the outside of the tagged region R2 by a moving operation by the operator. The observation target input receiving circuitry 231 receives that the mark M1 once received inside the tagged region R2 has been moved to the outside of the tagged region R2 thereafter. In such a case, it is determined in advance that a region of a CSF that flows out of the inside into the outside of the tagged region R2 should be designated as the CSF region serving as the observation target, in the same manner as the track of movement of the mark M1.

Figure 22B:
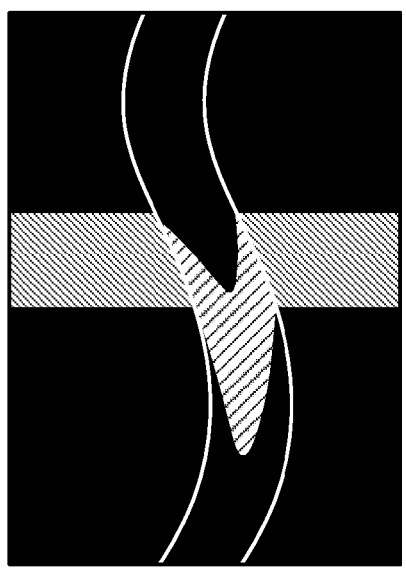

For example, the processed image generating circuitry 234 is notified of the input information received by the observation target input receiving circuitry 231. The processed image generating circuitry 234 generates a processed image to display the tagged CSF region extracted by the CSF region extraction circuitry 232 in "red", for example, as illustrated in FIG. 22B.

FIG. 23 and FIG. 24 illustrate the case where the tagged CSF flows out of the tagged region R2 in two directions, that is, an upper direction and a lower direction.

Figure 23A:
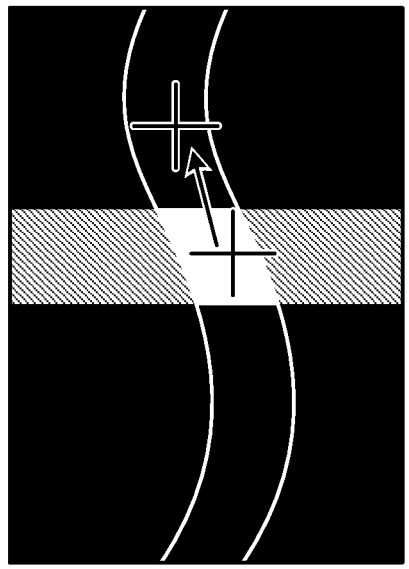

FIG. 23A illustrates an example where the mark M1, an input of which has been received inside the tagged region R2, has been moved to the upper side of the tagged region R2 by a moving operation by the operator. The observation target input receiving circuitry 231 receives that the mark M1 once received inside the tagged region R2 has been moved to the upper side of the tagged region R2 thereafter. In such a case, it is determined in advance that a region of a CSF that flows out of the inside to the upper side of the tagged region R2 should be designated as the CSF region serving as the observation target, in the same manner as the track of movement of the mark M1.

Figure 23B:
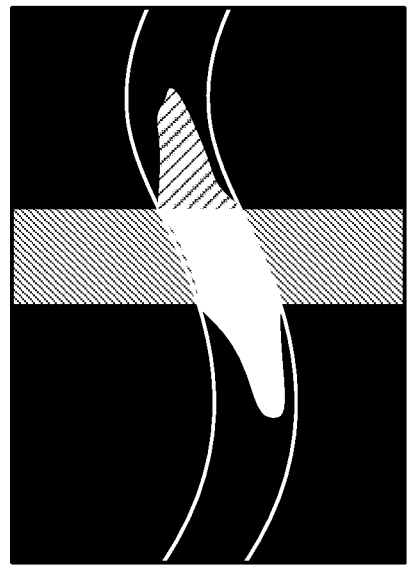

For example, the processed image generating circuitry 234 is notified of the input information received by the observation target input receiving circuitry 231. The processed image generating circuitry 234 designates the tagged CSF region that flows into the upper side of the tagged region R2 in the tagged CSF region extracted by the CSF region extraction circuitry 232, as illustrated in FIG. 23B. Thereafter, the processed image generating circuitry 234 generates a processed image to display the designated region in "red", for example, as illustrated in FIG. 23B.

Figure 24A:
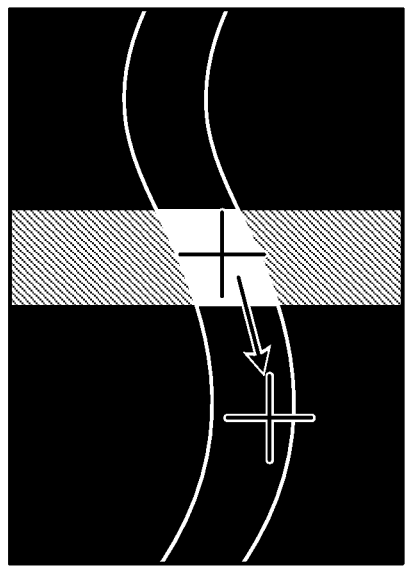

FIG. 24A illustrates an example where the mark M1, an input of which has been received inside the tagged region R2, has been moved to the lower side of the tagged region R2 by a moving operation by the operator. The observation target input receiving circuitry 231 receives that the mark M1 once received inside the tagged region R2 has been moved to the lower side of the tagged region R2 thereafter. In such a case, it is determined in advance that a region of a CSF that flows out of the inside to the lower side of the tagged region R2 should be designated as the CSF region serving as the observation target, in the same manner as the track of movement of the mark M1.

Figure 24B:
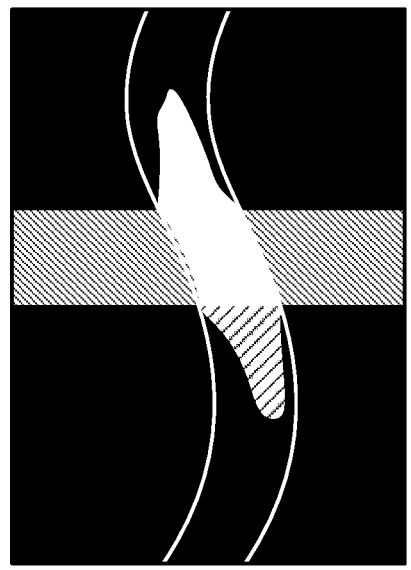

For example, the processed image generating circuitry 234 is notified of the input information received by the observation target input receiving circuitry 231. The processed image generating circuitry 234 designates the region that flows into the lower side of the tagged region R2 in the tagged CSF region extracted by the CSF region extraction circuitry 232, as illustrated in FIG. 24B. Thereafter, the processed image generating circuitry 234 generates a processed image to display the designated region in "red", for example, as illustrated in FIG. 24B.

FIG. 25 and FIG. 26 illustrate the case where the tagged CSF flows into the tagged region R2 from two directions, that is, an upper direction and a lower direction.

Figure 25A:
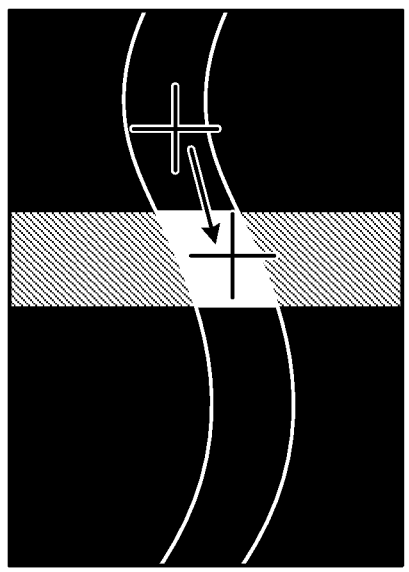

FIG. 25A illustrates an example where the mark M1, an input of which has been received on the upper side of the tagged region R2, has been moved to the inside of the tagged region R2 by a moving operation by the operator. The observation target input receiving circuitry 231 receives that the mark M1 once received on the upper side of the tagged region R2 has been moved to the inside of the tagged region R2 thereafter. In such a case, it is determined in advance that a region of a CSF that flows from the outside to the inside of the tagged region R2 should be designated as the CSF region serving as the observation target, in the same manner as the track of movement of the mark M1.

Figure 25B:
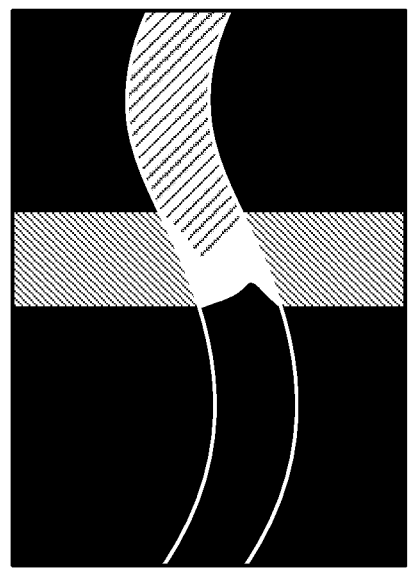

For example, the processed image generating circuitry 234 is notified of the input information received by the observation target input receiving circuitry 231. The processed image generating circuitry 234 designates the region that flows into the tagged region R2 from the upper side thereof and excludes the tagged CSF region, among the CSF form regions extracted by the CSF region extraction circuitry 232. Thereafter, the processed image generating circuitry 234 generates a processed image to display the designated region in "red", for example, as illustrated in FIG. 25B.

Figure 26A:
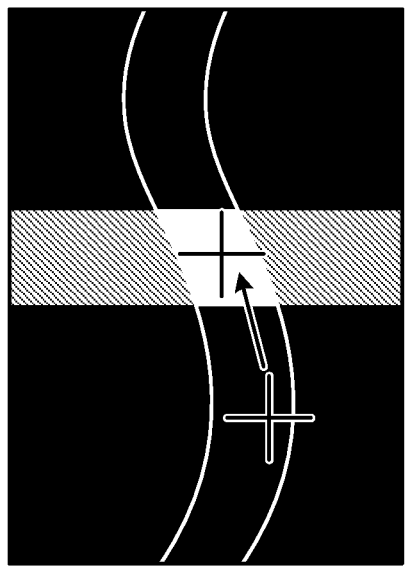

FIG. 26A illustrates an example where the mark M1, an input of which has been received on the lower side of the tagged region R2, has been moved to the inside of the tagged region R2 by a moving operation by the operator. The observation target input receiving circuitry 231 receives that the mark M1 once received on the lower side of the tagged region R2 has been moved to the inside of the tagged region R2 thereafter. In such a case, it is determined in advance that a region of a CSF that flows from the lower side to the inside of the tagged region R2 should be designated as the CSF region serving as the observation target, in the same manner as the track of movement of the mark M1.

Figure 26B:
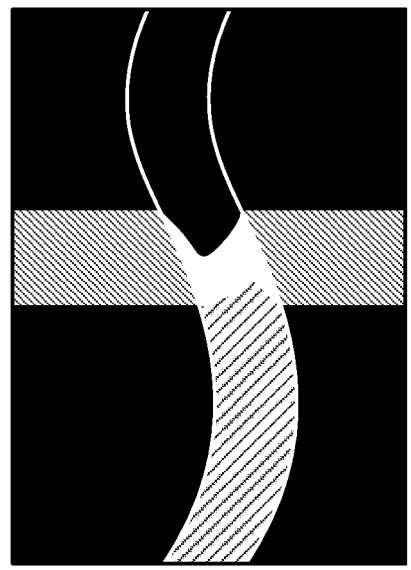

For example, the processed image generating circuitry 234 is notified of the input information received by the observation target input receiving circuitry 231. The processed image generating circuitry 234 designates the region that flows into the tagged region R2 from the lower side thereof and excludes the tagged CSF region, among the CSF form regions extracted by the CSF region extraction circuitry 232. Thereafter, the processed image generating circuitry 234 generates a processed image to display the designated region in "red", for example, as illustrated in FIG. 26B.

Next, FIG. 27 and FIG. 28 illustrate the case where the tagged CSF flows out of the tagged region R2 in a plurality of directions.

Figure 27A:
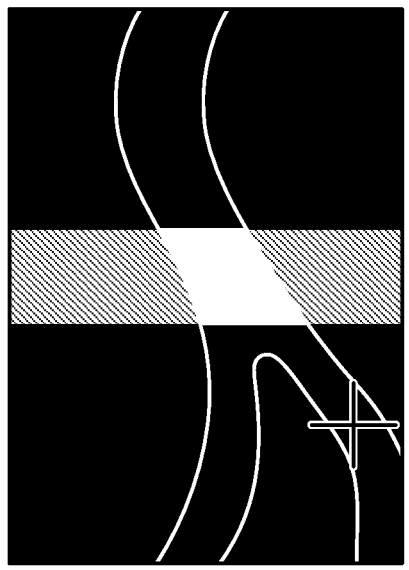

FIG. 27A illustrates an example where the observation target input receiving circuitry 231 receives an input of the mark M1 on the right path in the fluid paths that branch from the tagged region R2. For example, when target point information is input in one of a plurality of fluid paths, it is determined in advance that a region of a CSF that flows out of the tagged region R2 to the path should be designated as the CSF region serving as the observation target.

Figure 27B:
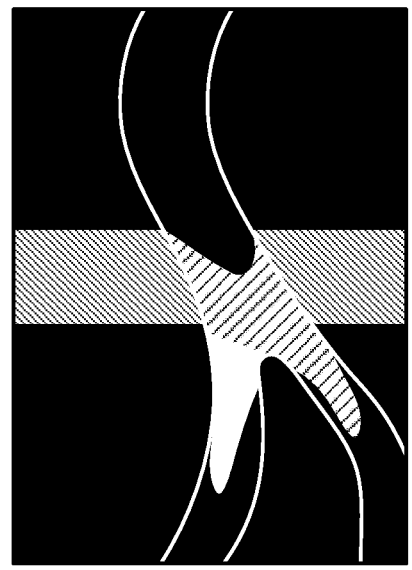

For example, the processed image generating circuitry 234 is notified of the input information received by the observation target input receiving circuitry 231. The processed image generating circuitry 234 generates a processed image to display the CSF region flowing into the right path in the tagged CSF region extracted by the CSF region extraction circuitry 232 in "red", for example, as illustrated in FIG. 27B.

Figure 28A:
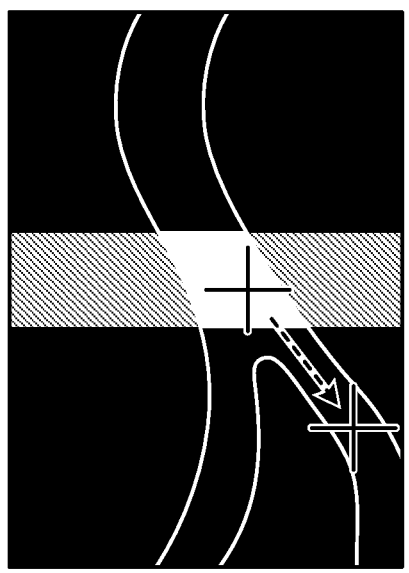

FIG. 28A illustrates an example where the mark M1, an input of which has been received inside the tagged region R2, has been moved onto the right path in the fluid paths branching from the tagged region R2 by a moving operation by the operator. The observation target input receiving circuitry 231 receives that the mark M1 once received inside the tagged region R2 has been moved onto a certain path thereafter. In such a case, it is determined in advance that a region of a CSF that flows out of the inside of the tagged region R2 to the path should be designated as the CSF region serving as the observation target, in the same manner as the track of movement of the mark M1.

Figure 28B:

For example, the processed image generating circuitry 234 is notified of the input information received by the observation target input receiving circuitry 231. The processed image generating circuitry 234 generates a processed image to display the CSF region flowing into the right path in the tagged CSF region extracted by the CSF region extraction circuitry 232 in "red", for example, as illustrated in FIG. 28B.

Figure 29:
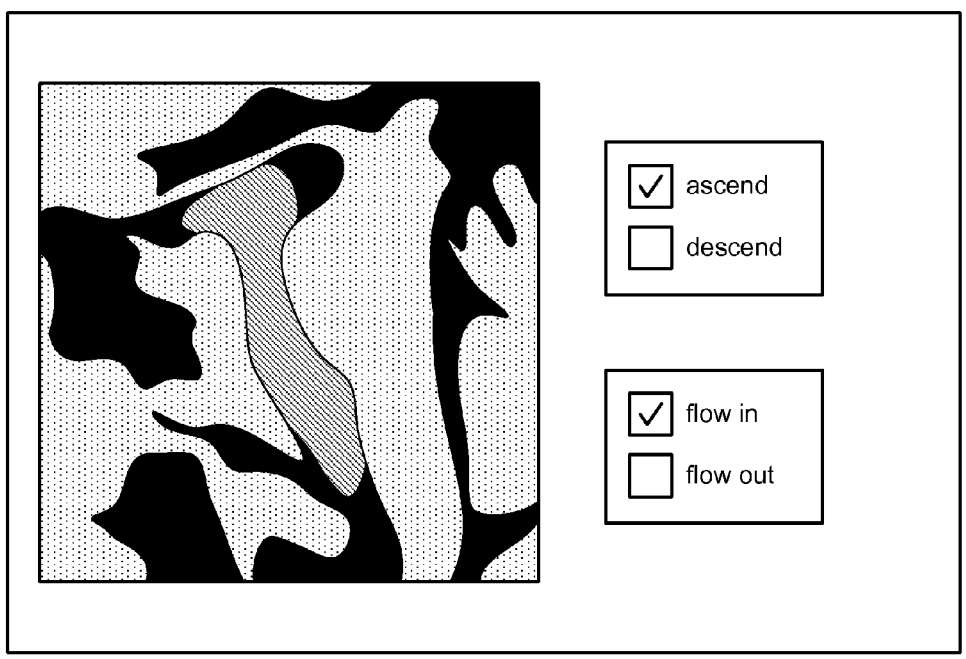
FIG. 29 is a diagram for explaining input of target point information in another embodiment.
Figure 30:
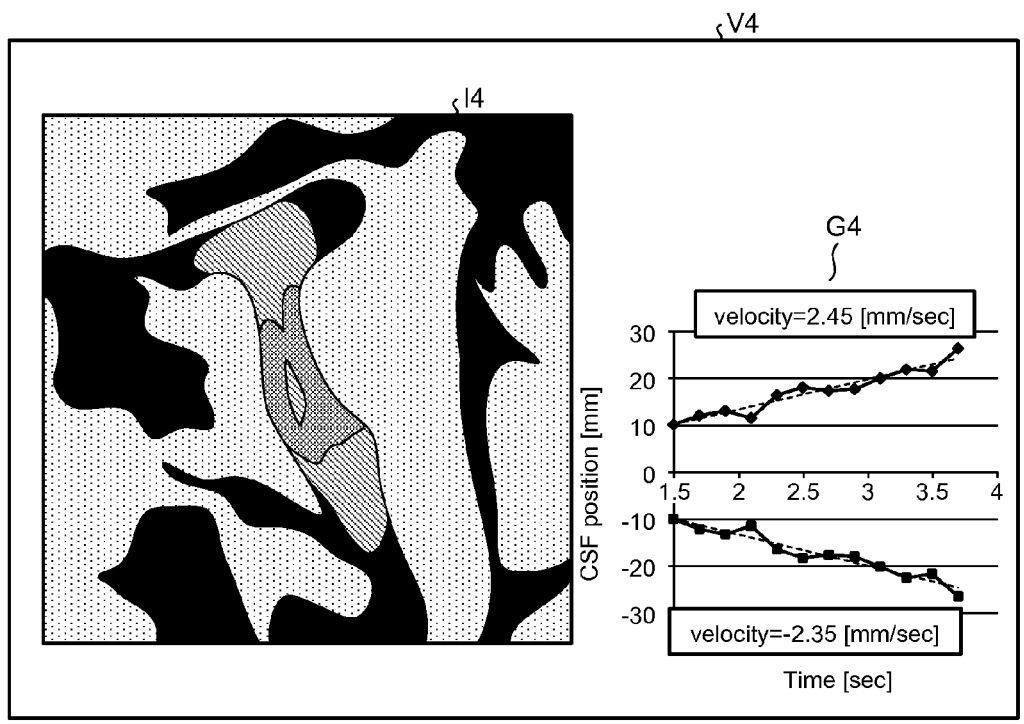
FIG. 30 is a diagram for explaining an analysis result display screen in the second embodiment.

The observation target input receiving circuitry 231 may receive an input of designation information of similar contents in the form of button selection. FIG. 29 is a diagram for explaining an input of target point information in another embodiment. For example, the observation target input receiving circuitry 231 may cause buttons to be displayed for selection of "ascend (upward)", "descend (downward)", "flow in (flowing into the tagged region R2)", and "flow out (flowing out of the tagged region R2)" as the GUI, to receive an input from the operator. FIG. 30 is a diagram for explaining an analysis result display screen in the second embodiment. An analysis result display screen V4 displays a processed image I4 and a graph G4 side by side.

Other Embodiments

Embodiments are not limited to the embodiments above.
(Method for Designating Observation Target Region)

Figure 31:
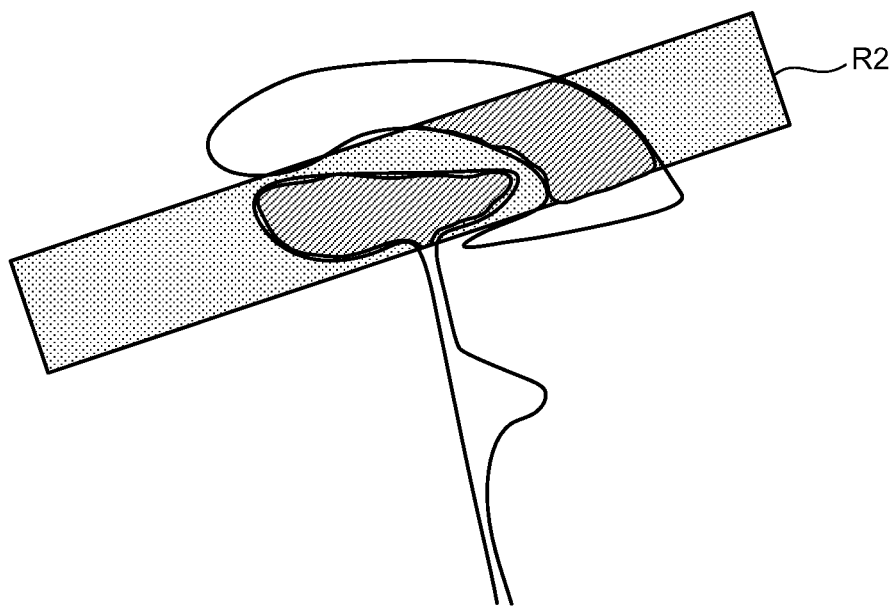
FIG. 31, FIG. 32 and FIG. 33 are explanatory drawings of a method for designating an observation target region in another embodiment.
Figure 32:
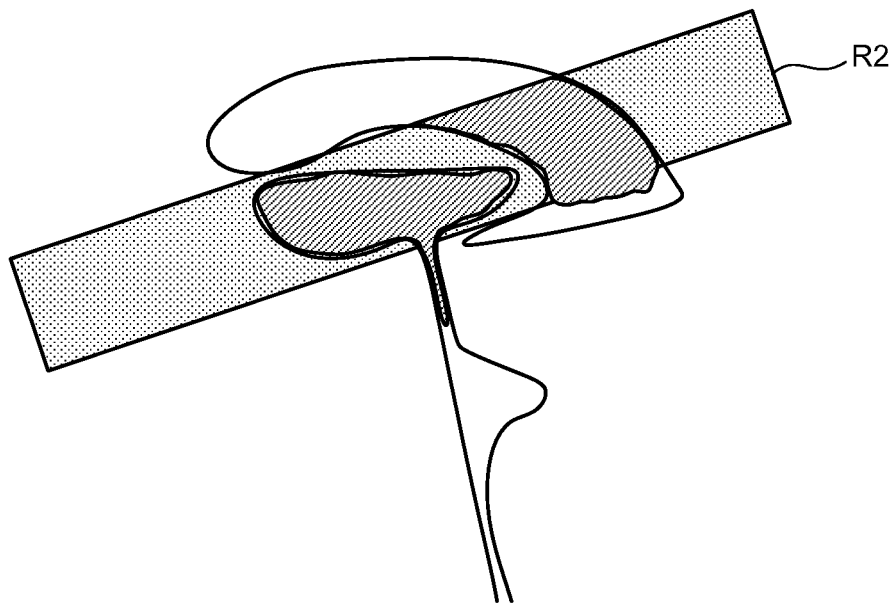
Figure 33:
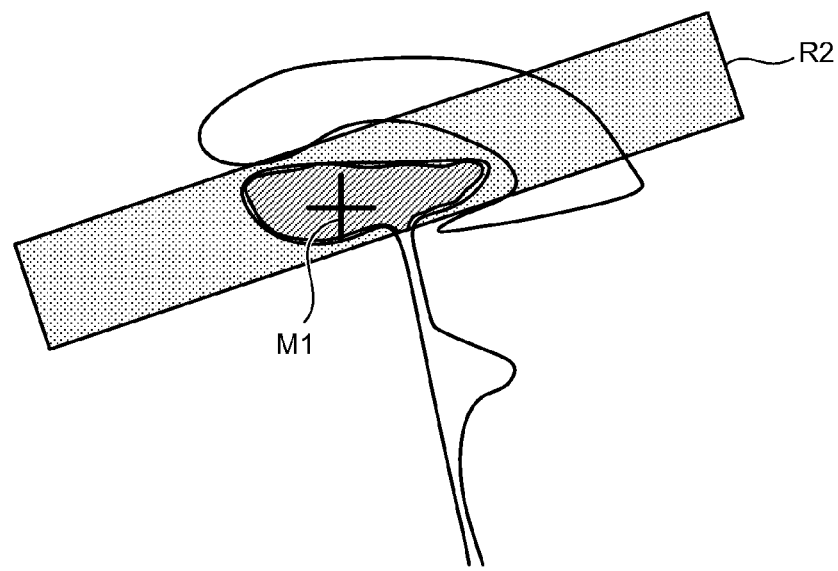

The following is an explanation of some variations of the method for designating the observation target region. FIG. 31 to FIG. 33 are diagrams for explaining the method for designating the observation target region in another embodiment. As illustrated in FIG. 31, for example, the operator may require the tagged CSF region included in the tagged region R2 as the observation target region. In such a case, designation of the observation target region may be omitted. The CSF region extraction circuitry 232 extracts the tagged region R2 from the CSF image using, for example, the setting information of the tagged region R2 attached to the CSF image group. Thereafter, the CSF region extraction circuitry 232 extracts the tagged CSF region from the tagged region R2 using a difference in signal value between the tagged CSF region and the other regions. The other regions are regions that is included in the tagged region R2 and not a CSF (such as a cerebral parenchyma region), non-tagged regions such as the cerebral aqueduct and the fourth ventricle, or cerebral parenchyma regions not illustrated. The processed image generating circuitry 234 generates a processed image to display the tagged CSF region extracted by the CSF region extraction circuitry 232 and included in the tagged region R2 in "red", for example.

In addition, as illustrated in FIG. 32, the operator may require the tagged CSF region including not only the inside of the tagged region R2 but also the outside of the tagged region R2, as the observation target region. Also in such a case, designation of the observation target region may be omitted. The CSF region extraction circuitry 232 extracts the tagged region R2 from the CSF image using, for example, the setting information of the tagged region R2 attached to the CSF image group. Thereafter, the CSF region extraction circuitry 232 extracts the tagged CSF region from the tagged region R2 using a difference in signal value between the tagged CSF region and the other regions. The CSF region extraction circuitry 232 determines a characteristic amount of the signal value of the extracted tagged CSF region, and extracts pixels having a characteristic amount similar to the characteristic amount determined from the tagged CSF region for the pixels outside the tagged region R2, as the observation target region. The processed image generating circuitry 234 thereafter generates a processed image to display the tagged CSF region extracted by the CSF region extraction circuitry 232 and located inside and outside the tagged region R2 in "red", for example.

The index derivation circuitry 233 can designated a position having the largest distance from the tagged region R2 in the observation target region extracted by the CSF region extraction circuitry 232, as the distal end CSF position. In such a case, for example, the index derivation circuitry 233 can determine the distance from the tagged region R2 with an axis in the direction of a perpendicular line that perpendicularly extends from the rectangular tagged region R2. In the determination, the index derivation circuitry 233 uses rotational information that indicates the orientation of the tagged region R2.

In addition, as illustrated in FIG. 33, for example, the operator may require only the tagged CSF region in a predetermined region (for example, the tagged CSF region in the third ventricle) in the tagged CSF region included in the tagged region R2, as the observation target region. In such a case, as illustrated in FIG. 33, the observation target input receiving circuitry 231 receives an input of the mark M1 that designates a predetermined position in the CSF image. The CSF region extraction circuitry 232 extracts the tagged region R2 from the CSF image using, for example, the setting information of the tagged region R2 attached to the CSF image group. Thereafter, the CSF region extraction circuitry 232 extracts the tagged CSF regions from the tagged region R2 using a difference in signal value between the tagged CSF region and the other regions. The CSF region extraction circuitry 232 thereafter extracts the tagged CSF region including the mark M1, an input of which has been received by the observation target input receiving circuitry 231, in the plurality of tagged CSF regions extracted from the tagged region R2, as the observation target region. The processed image generating circuitry 234 generates a processed image to display the tagged CSF region extracted by the CSF region extraction circuitry 232 in "red", for example.

Alternatively, for example, the CSF region extraction circuitry 232 may analyze the tagged region R2 extracted from the CSF image by k-average method or discriminant analysis method, and extract the region including the mark M1, an input of which has been received by the observation target input receiving circuitry 231, as the observation target region.

Alternatively, for example, the CSF region extraction circuitry 232 may determine a characteristic amount of the signal intensity for pixels corresponding to the mark M1, an input of which has been received by the observation target input receiving circuitry 231, and extract a region having the same value as, or a value close to, the characteristic amount as the observation target region.

For example, the CSF region extraction circuitry 232 may extract the observation target region by operator's manual designation via the input circuitry 211. For example, the CSF region extraction circuitry 232 may cause the CSF image group to be displayed on the display 212, and receive designation of the observation target region on each of the CSF images by a manual operation by the operator.

The observation target region extracted by the CSF region extraction circuitry 232 as described above is used for, for example, processing performed by the index derivation circuitry 233 and processing performed by the processed image generating circuitry 234.

(Imaging Cross Section)

The embodiments above illustrate the case where the MRI apparatus 100 images the sagittal plane of the brain as the CSF image, but the embodiments are not limited thereto. The MRI apparatus 100 can image any imaging cross section for any imaging region. Also in such a case, the image processing apparatus 200 can apply the various processing above in the same manner.

Figure 34:
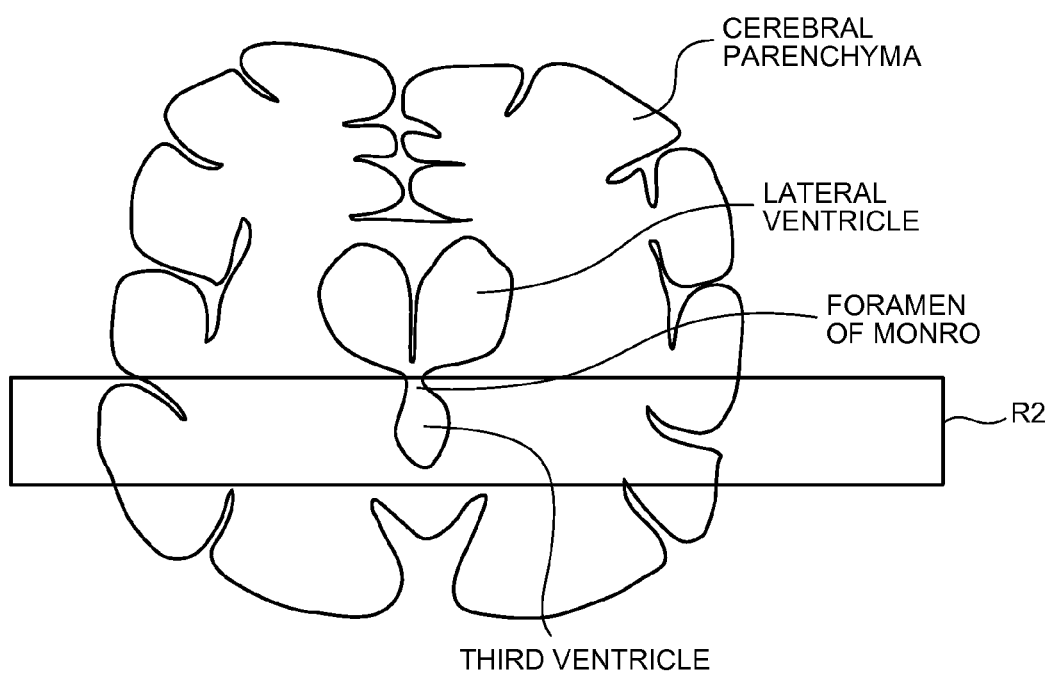
FIG. 34 is a diagram illustrating an imaging cross section in another embodiment.

FIG. 34 is a diagram illustrating an imaging cross section in another embodiment. For example, the MRI apparatus 100 may image a plane (referred to as "coronal section" or "coronal plane") that is parallel with both the forehead and the body axis of the subject P, as the CSF image, as illustrated in FIG. 34. The CSF image of the coronal plane illustrated in FIG. 34 includes characteristic regions in the brain in which CSF exists, in addition to the cerebral parenchyma, such as the lateral ventricle, the foramen of Monro, and the third ventricle. In the case of the example illustrated in FIG. 34, the tagged region R2 is set on, for example, the third ventricle serving as the starting point from which the CSF flows out.

As a result, the CSF that flows out of the third ventricle to the lateral ventricle can be visually recognized in the obtained CSF image. Accordingly, the MRI apparatus 100 can extract a tagged CSF region from the CSF image, designate the CSF position and the area in the extracted tagged CSF region, and calculate indexes that indicate the dynamic state of the CSF, in the same manner as the embodiments above. In other words, the MRI apparatus 100 should set the imaging cross section such that the CSF can be visually recognized along the moving direction or the dispersion direction of the CSF.

As another example, the MRI apparatus 100 may image a sagittal plane, a coronal plane, or a plane (referred to as "body axis cross section" or "axial plane") that is perpendicular to the body axis of the subject, for the spine or the cervical spine. Also in such a case, the MRI apparatus 100 should set the imaging cross section such that the CSF can be visually recognized along the moving direction or the dispersion direction of the CSF, in the same manner. Specifically, the MRI apparatus 100 is not always required to set the imaging cross section to include all the lateral ventricle, the foramen of Monro, and the third ventricle, but may set the imaging cross section to include, for example, only the lateral ventricle. For example, when the spine is imaged, the MRI apparatus 100 should set a proper imaging cross section, an imaging region, and a tagged region to enable visual recognition of the CSF along the moving direction or the dispersion direction of the CSF.

(Others)

The embodiments above illustrate the structure in which the image processing apparatus 200 of the image processing system 10 performs various processing for evaluation of the dynamic state of the CSF, but the embodiments are not limited thereto. For example, the MRI apparatus 100 alone may perform acquisition of the CSF image group and various processing for evaluation of the dynamic state of the CSF. In such a case, for example, the calculator 130 of the MRI apparatus 100 may include the various units (such as the observation target input receiving circuitry 231, the CSF region extraction circuitry 232, the index derivation circuitry 233, the processed image generating circuitry 234, and the display controlling circuitry 235) that are included in the image processing apparatus 200 in the explanation above.

The embodiments above illustrate the case of using MR images that are imaged by the MRI apparatus 100, but the embodiments are not limited thereto. For example, the various processing above are also applicable in the same manner to the cases of using images that are imaged by other medical image diagnostic apparatuses, such as an X-ray computed tomography (CT) apparatus, an X-ray diagnostic apparatus, and an ultrasonic diagnostic apparatus. Specifically, the various processing above are also applicable in the same manner to the cases where an image group of a fluid flowing in the subject is imaged by other medical image diagnostic apparatus.

In addition, the embodiments above illustrate a CSF as an example of the fluid that flows in the subject, but the embodiments are not limited thereto. For example, the fluid may be blood, pancreatic juice, or lymph.

(Computer Program)

Instructions illustrated in the processing procedures in the embodiments above may be performed based on a computer program serving as software. A general-purpose computer stores therein the computer program in advance, and reading the computer program can produce effects similar to the effects obtained by the MRI apparatus 100 according to the embodiments above. The instructions described in the embodiments above are stored in a magnetic disk, an optical disk, a semiconductor memory, or other similar storage medium, as a computer program that can be executed by a computer. The storage form thereof may be any form, as long as the storage medium is a storage medium that is readable by a computer or an incorporation system. Operations similar to those of the MRI apparatus 100 according to the embodiments above can be implemented by reading the computer program from the storage medium by a computer, and causing a CPU to execute the instructions described in the computer program based on the computer program. As a matter of course, a computer may obtain or read the computer program via a network, when the computer obtains or reads the computer program.

In addition, part of the processing to implement the embodiments above may be executed by an operating system (OS) that operates on the computer, database management software, or middleware such as a network, based on the instructions of the computer program installed from a storage medium into the computer or the incorporation system.

The storage medium in the embodiments is not limited to a medium independent of the computer or the incorporation system, but also includes a storage medium that stores or temporarily stores therein the computer program transmitted through a LAN or the Internet and downloaded. The computer program to implement the processing of the embodiments above may be stored on a computer (server) connected to a network such as the Internet, and downloaded by a computer (client) via the network. In addition, the storage medium is not limited to one storage medium, but the storage medium in the embodiments also includes the case of executing the processing in the embodiments above from a plurality of storage media, and the structure of the medium may be any structure.

The computer or the incorporation system in the embodiments perform each of the processing in the embodiments above based on the computer program stored in a storage medium, and may have any structure such as an apparatus formed of a personal computer or a microcomputer, and a system in which a plurality of apparatuses are connected via a network. The computer in the embodiments is not limited to a personal computer, but also includes an arithmetic processing unit included in an information processing apparatus and a microcomputer, and serves as a general term for apparatuses and devices that can implement the functions in the embodiments above with the computer program.

The image processing apparatus and the magnetic resonance imaging apparatus according to at least one of the embodiments described above enable proper provision of information for evaluating the dynamic state of a fluid.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a processor; and
a memory that stores processor-executable instructions that, when executed by the processor, cause the processor to:
receive an input of information designating an observation target;
extract, from each of magnetic resonance(MR) images included in an MR image group collected by applying a tagging pulse to a region where a fluid flows, a group of spatial sub-regions of the fluid within the images;
analyze, by an analyzing method associated with the observation target, the group of spatial sub-regions extracted from each of the MR images, thereby deriving an index indicating a dynamic state of the fluid; and
cause the index to be displayed on a display.

2. The apparatus according to claim 1, wherein
the processor-executable instructions further cause the processor to:
receive information on an anatomical region as the information designating the observation target and
analyze, by the analyzing method associated with the anatomical region, the group of spatial sub-regions of the fluid, to derive the index.

3. The apparatus according to claim 2, wherein
the processor-executable instructions further cause the processor to:
cause a list of anatomical region names to be displayed on the display, and
receive a selection for the list.

4. The apparatus according to claim 1, wherein the analyzing method includes a first analyzing method of tracking temporal displacement of one position in a spatial region of the fluid, thereby deriving an index indicating the dynamic state of the fluid for the position.

5. The apparatus according to claim 4, wherein
the analyzing method further includes a second analyzing method of tracking temporal displacements of a plurality of positions in a spatial region of the fluid, thereby deriving an index indicating the dynamic state of the fluid for each of the plurality of positions, and the memory stores processor-executable instructions that, when executed by the processor, cause the processor to:
select the first analyzing method or the second analyzing method according to the observation target, to derive the index.

6. The apparatus according to claim 2,
wherein the processor-executable instructions further cause the processor to change a color of a spatial region designated as an observation target region on the MR images.

7. The apparatus according to claim 2,
wherein the processor-executable instructions further cause the processor to receive an input of information designating an observation target region that is the anatomical region.

8. The apparatus according to claim 7,
wherein the processor-executable instructions further cause the processor to designate fluid paths according as a transition of a position of a mark due to a moving operation by an operator.

9. A magnetic resonance imaging apparatus comprising:
an MRI system including a controller to execute a pulse sequence to apply a tagging pulse to a region where a cerebrospinal fluid flows, thereby acquiring a group of MR (Magnetic Resonance) images;
a processor; and
a memory that stores processor-executable instructions that, when executed by the processor, cause the processor to:
receive an input of information designating an observation target;
extract, from each of MR images included in the group of MR images, a group of spatial sub-regions of the cerebrospinal fluid within the images;
analyze, by an analyzing method associated with the observation target, the group of spatial sub-regions extracted from each of the MR images, thereby deriving an index indicating a dynamic state of the cerebrospinal fluid; and
cause the index to be displayed on a display.

10. An image processing method comprising:
receiving an input of information designating an observation target;
extracting, from each of magnetic resonance(MR) images included in an MR image group collected by applying a tagging pulse to a region where a fluid flows, a group of spatial sub-regions of the fluid within the images;
analyzing, by an analyzing method associated with the observation target, the group of spatial sub-regions extracted from each of the MR images, thereby deriving an index indicating a dynamic state of the fluid; and
causing the index to be displayed on a display.

* * * * *